United States Patent
Cermak

(10) Patent No.: US 10,507,038 B2
(45) Date of Patent: Dec. 17, 2019

(54) NEEDLE GUIDE DEVICES FOR MOUNTING ON IMAGING TRANSDUCERS OR ADAPTORS ON IMAGING TRANSDUCER, IMAGING TRANSDUCERS FOR MOUNTING NEEDLE GUIDE DEVICES AND ADAPTORS FOR IMAGING TRANSDUCERS FOR MOUNTING NEEDLE GUIDE DEVICES THEREON

(71) Applicant: CIVCO Medical Instruments Co., Inc., Kalona, IA (US)

(72) Inventor: Craig Joseph Cermak, Riverside, IA (US)

(73) Assignee: CIVCO MEDICAL INSTRUMENTS CO., INC., Kalona, IA (US)

( * ) Notice: Subject to any disclaimer, the term of this patent is extended or adjusted under 35 U.S.C. 154(b) by 511 days.

(21) Appl. No.: 14/930,077

(22) Filed: Nov. 2, 2015

(65) Prior Publication Data

US 2016/0128719 A1   May 12, 2016

Related U.S. Application Data

(60) Provisional application No. 62/078,744, filed on Nov. 12, 2014, provisional application No. 62/160,776, filed on May 13, 2015.

(51) Int. Cl.
   *A61B 17/34*   (2006.01)
   *A61B 8/08*   (2006.01)
   *A61B 8/00*   (2006.01)

(52) U.S. Cl.
   CPC ........ *A61B 17/3403* (2013.01); *A61B 8/0841* (2013.01); *A61B 8/4455* (2013.01);
   (Continued)

(58) Field of Classification Search
   CPC ........ A61B 17/3403; A61B 2017/3407; A61B 8/42; A61B 8/4209; A61B 8/4272; A61B 8/4281
   See application file for complete search history.

(56) References Cited

U.S. PATENT DOCUMENTS 4,469,106 A   9/1984   Harui
4,576,175 A   3/1986   Epstein
(Continued)

FOREIGN PATENT DOCUMENTS

DE   102010008491 A1   8/2011
EP   1552792 A1   7/2005
JP   H01 97440 A   4/1989

OTHER PUBLICATIONS

Partial European Search Report for EP 15003185 completed Apr. 5, 2016.

*Primary Examiner* — Hien N Nguyen
(74) *Attorney, Agent, or Firm* — Snyder, Clark, Lesch & Chung, LLP

(57) ABSTRACT

A needle guide device for releasable mounting on an imaging transducer or on an adaptor bracket on an imaging transducer is disclosed. The needle guide device includes a universal lockable mounting member which is configured for slidable releasable engagement with a coupling member on a specially constructed imaging transducer or on a conventional imaging transducer onto which a specially constructed adaptor is mounted. The needle guide device makes use of a slidable mounting member to cooperate with the coupling member. The needle guide device is adjustable to establish various selectable angular trajectories for a needle and has a low profile form factor to result in the creation of a minimal blind zone when mounted on the transducer and even if establishing a large angle for shallow needle penetration.

10 Claims, 13 Drawing Sheets

(52) U.S. Cl.
CPC ............... *A61B 2017/3405* (2013.01); *A61B 2017/3413* (2013.01)

(56) References Cited

U.S. PATENT DOCUMENTS

| | | | |
|---|---|---|---|
| 4,899,756 A | 2/1990 | Sonek | |
| 5,052,396 A | 10/1991 | Wedel et al. | |
| 5,076,279 A | 12/1991 | Arenson et al. | |
| 5,235,987 A | 8/1993 | Wolfe | |
| 5,623,931 A | 4/1997 | Wung et al. | |
| 5,758,650 A | 6/1998 | Miller et al. | |
| 5,924,992 A | 7/1999 | Park et al. | |
| 5,941,889 A | 8/1999 | Cermak | |
| D424,693 S | 5/2000 | Pruter | |
| 6,203,499 B1 | 3/2001 | Imling et al. | |
| 6,296,614 B1 | 10/2001 | Pruter | |
| 6,361,499 B1 * | 3/2002 | Bates | A61B 8/0833 600/461 |
| 6,368,280 B1 | 4/2002 | Cermak et al. | |
| 6,379,307 B1 | 4/2002 | Filly et al. | |
| 6,485,426 B2 | 11/2002 | Sandhu | |
| 6,884,219 B1 | 4/2005 | Pruter | |
| 7,022,082 B2 | 4/2006 | Sonek | |
| 7,087,024 B1 | 8/2006 | Pruter | |
| 7,351,205 B2 | 4/2008 | Szezech et al. | |
| 7,452,331 B1 | 11/2008 | Pruter | |
| 7,588,541 B2 | 9/2009 | Floyd et al. | |
| 7,635,336 B1 | 12/2009 | Pruter | |
| 7,691,066 B2 | 4/2010 | Kosaku | |
| 7,909,815 B2 | 3/2011 | Whitmore, III et al. | |
| 7,926,776 B2 | 4/2011 | Cermak | |
| 7,959,573 B2 | 6/2011 | Furia | |
| 8,073,529 B2 | 12/2011 | Cermak et al. | |
| 8,137,281 B2 | 3/2012 | Huang et al. | |
| 8,216,149 B2 | 7/2012 | Oonuki et al. | |
| 8,401,617 B2 | 3/2013 | Whitmore, III et al. | |
| 8,430,889 B2 | 4/2013 | Zeng et al. | |
| 8,747,324 B1 * | 6/2014 | Pruter | A61B 8/0833 24/327 |
| 2003/0171680 A1 | 9/2003 | Paltieli | |
| 2005/0059891 A1 | 3/2005 | Kosaku | |
| 2006/0129046 A1 | 6/2006 | Stevens et al. | |
| 2007/0038113 A1 | 2/2007 | Oonuki | |
| 2007/0049822 A1 | 3/2007 | Bunce et al. | |
| 2009/0143684 A1 | 6/2009 | Cermak et al. | |
| 2010/0082040 A1 * | 4/2010 | Sahni | A61B 17/3403 606/130 |
| 2010/0168766 A1 | 7/2010 | Zeng | |
| 2012/0165679 A1 | 6/2012 | Orome et al. | |
| 2012/0259221 A1 | 10/2012 | Sheldon | |
| 2013/0150714 A1 | 7/2013 | Howlett | |

\* cited by examiner

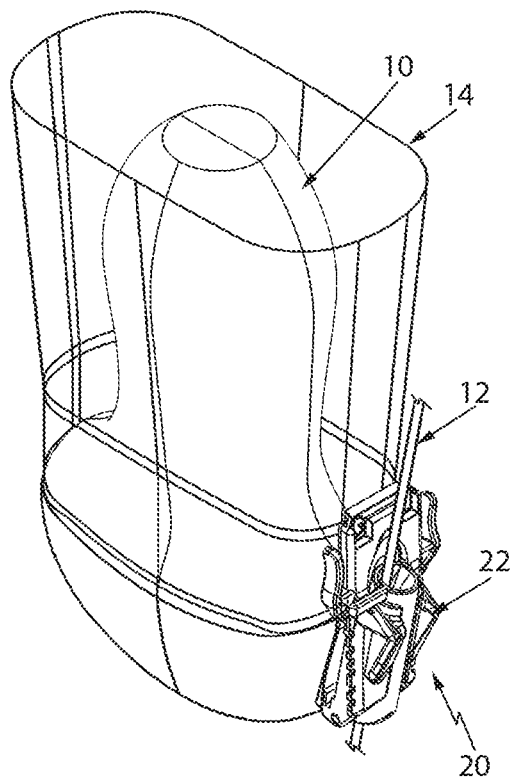
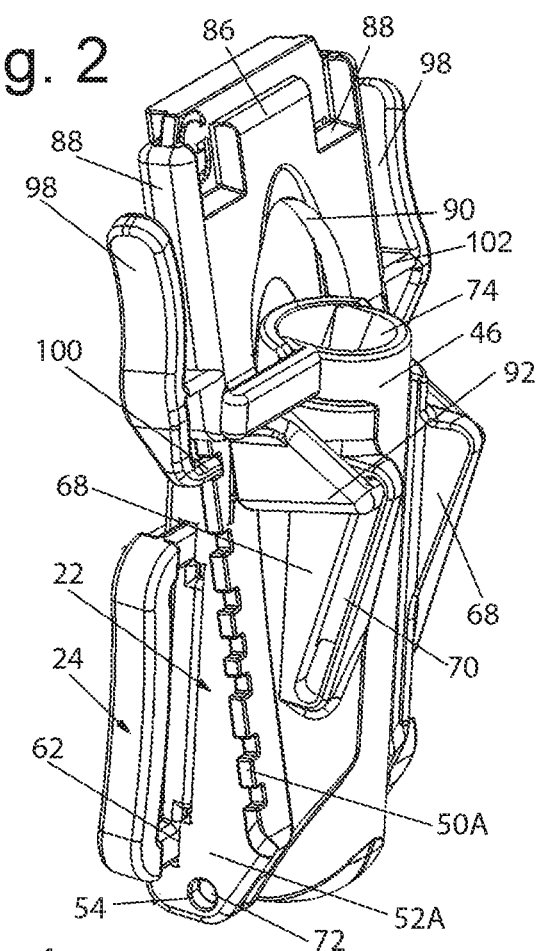
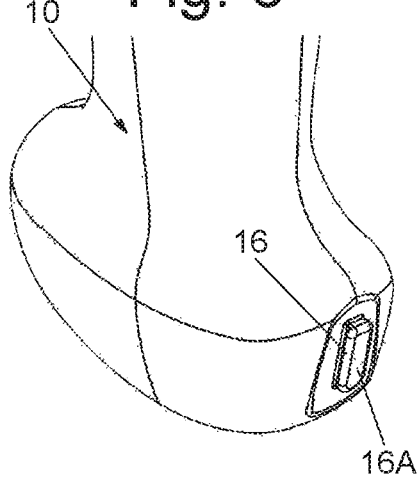
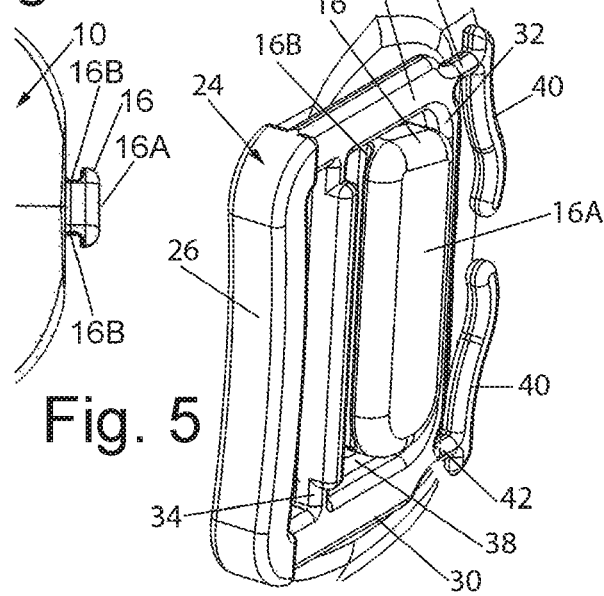

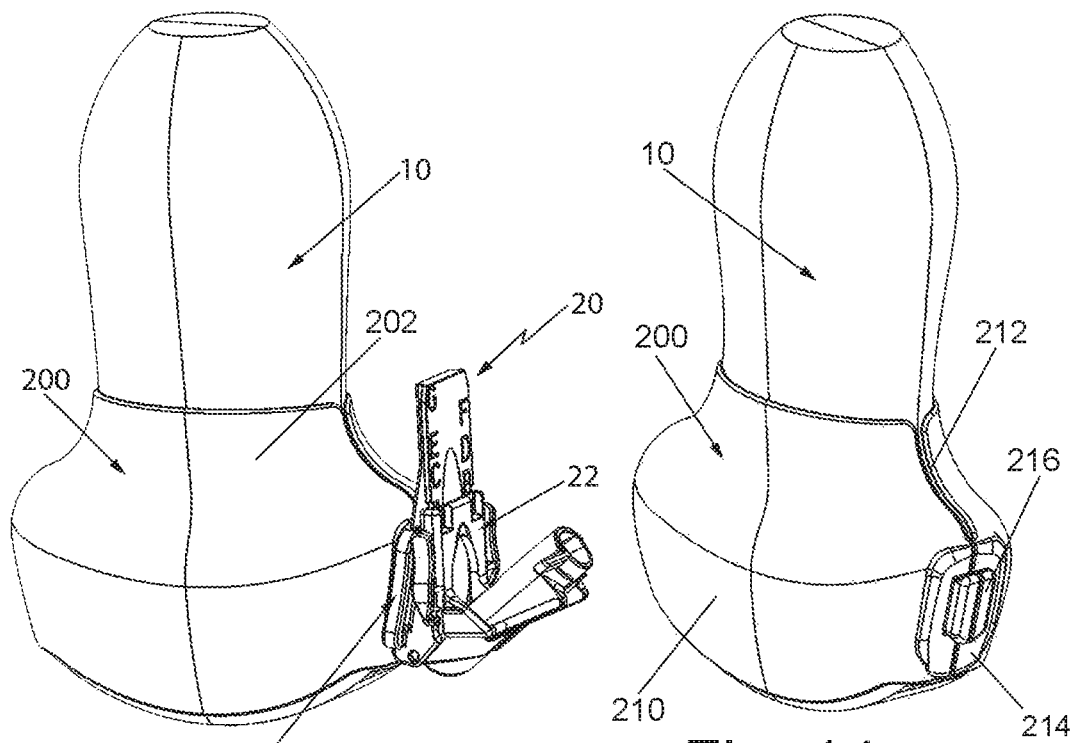
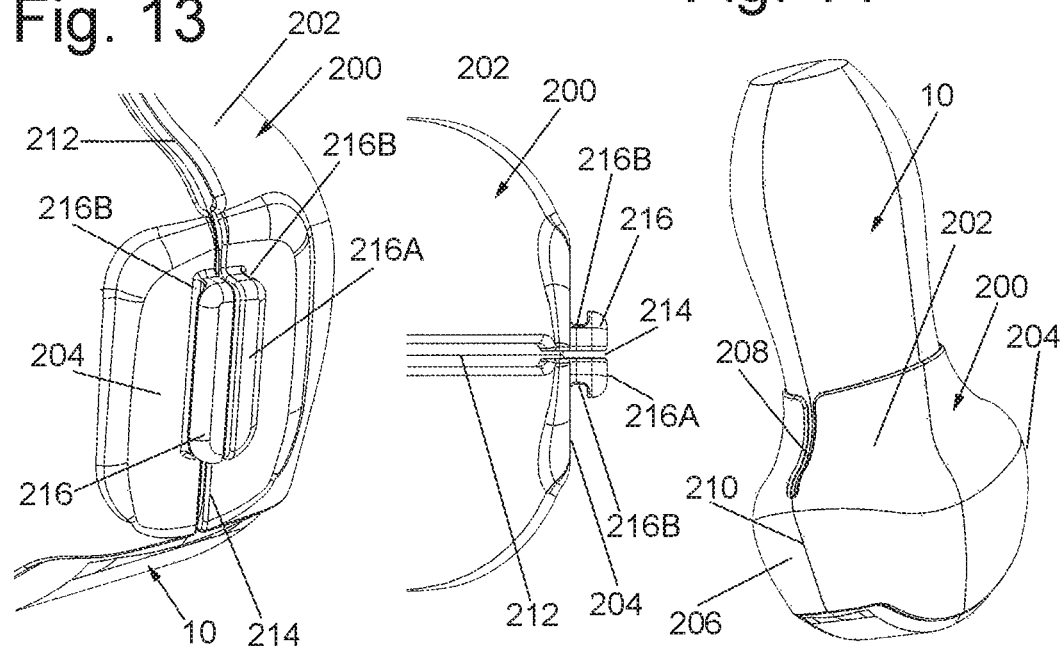

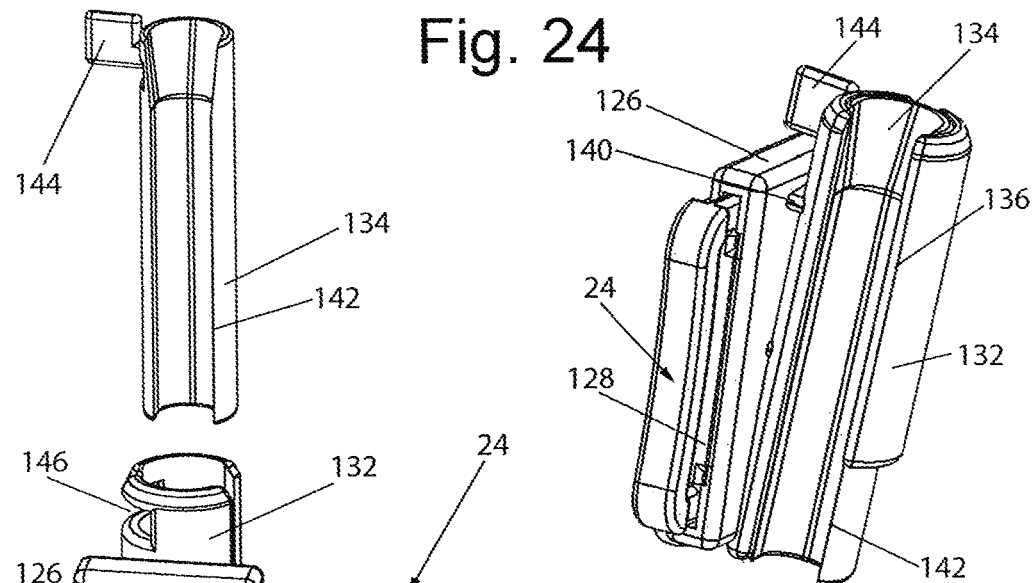
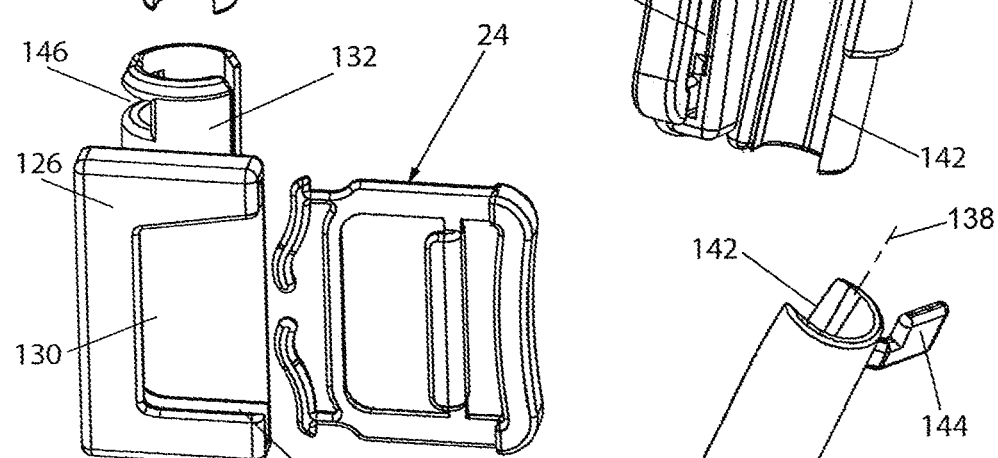
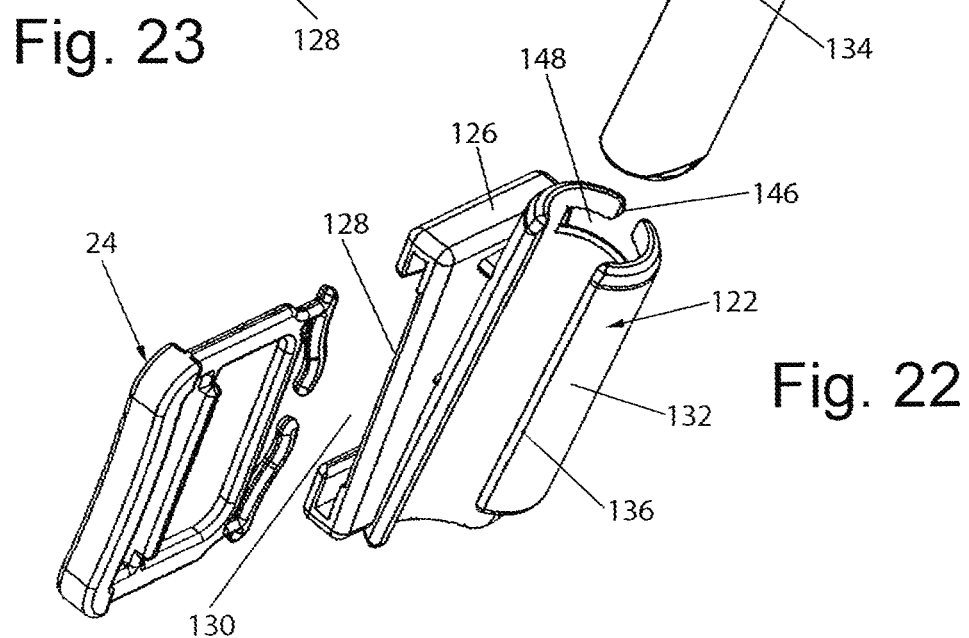

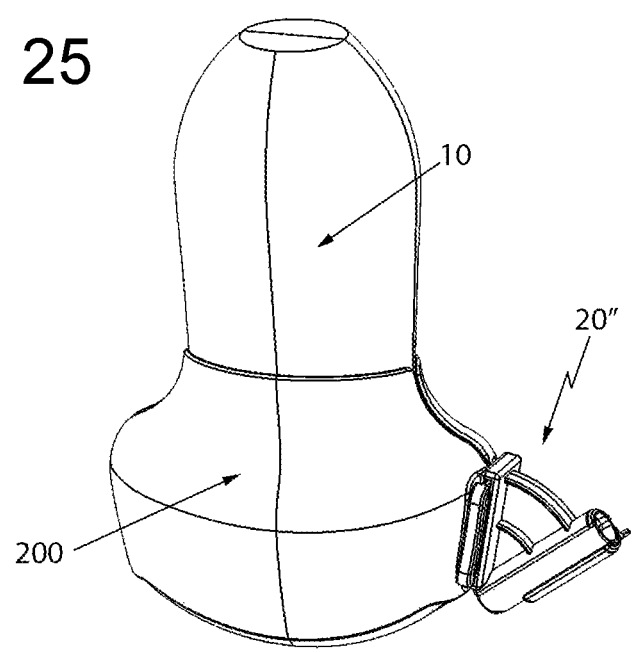

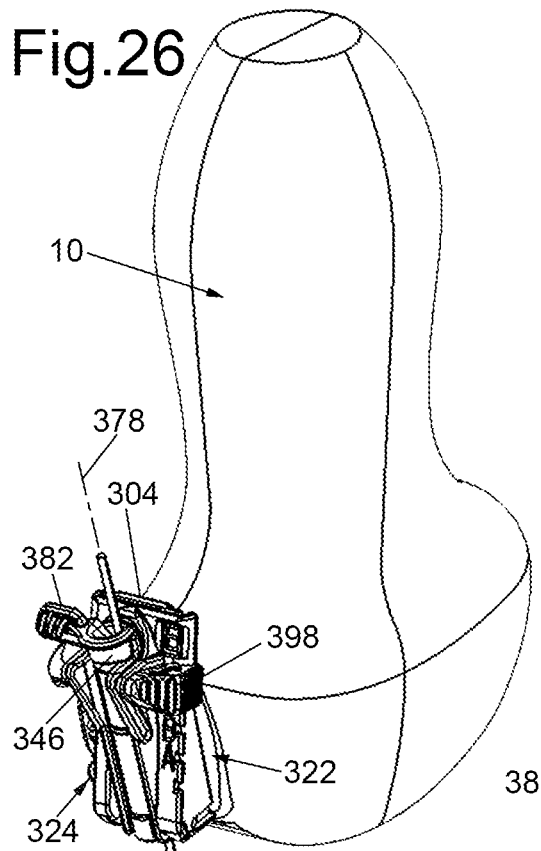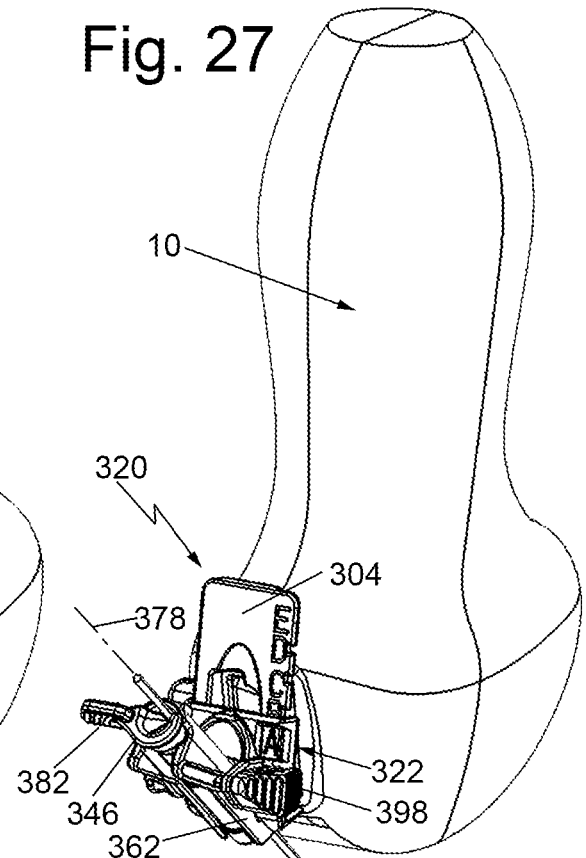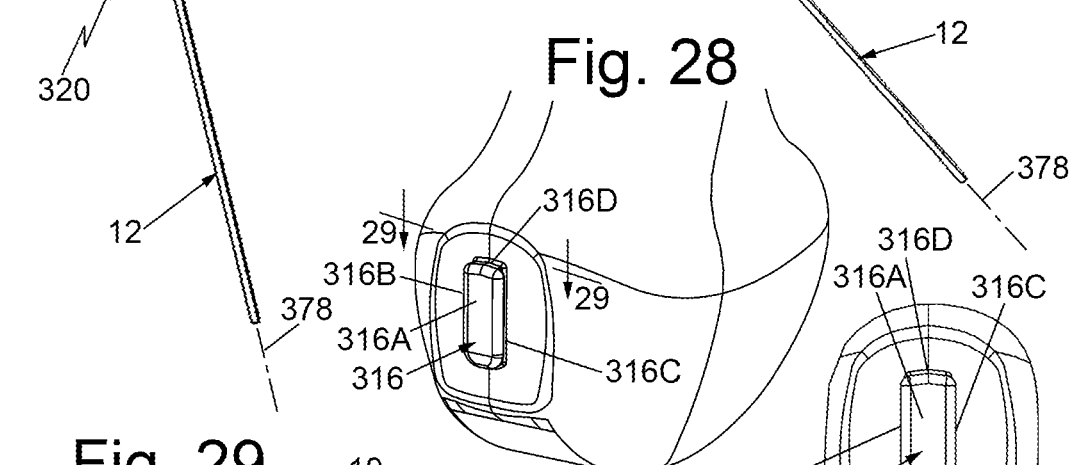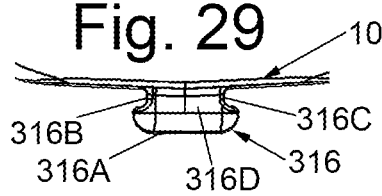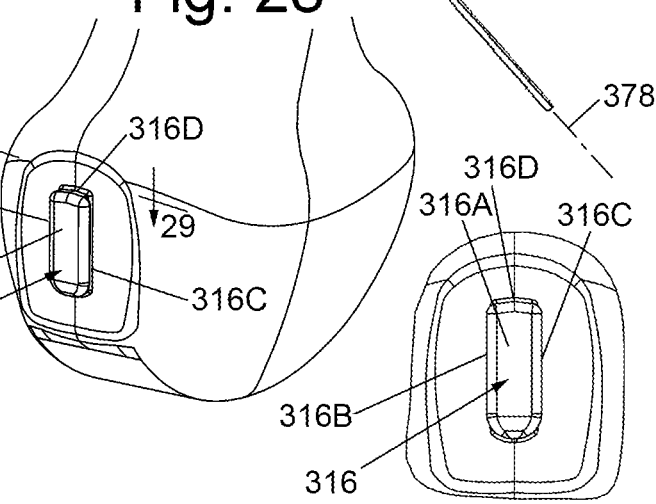

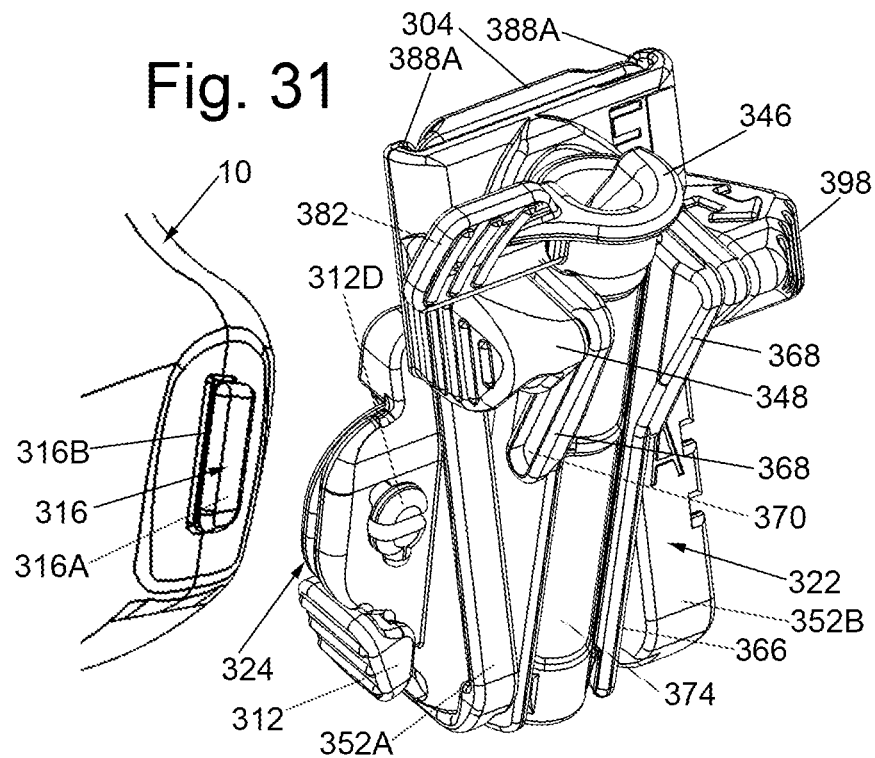
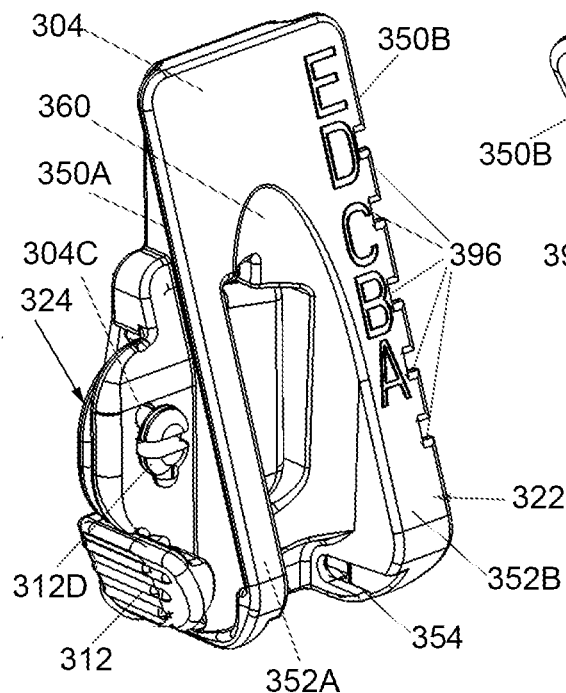
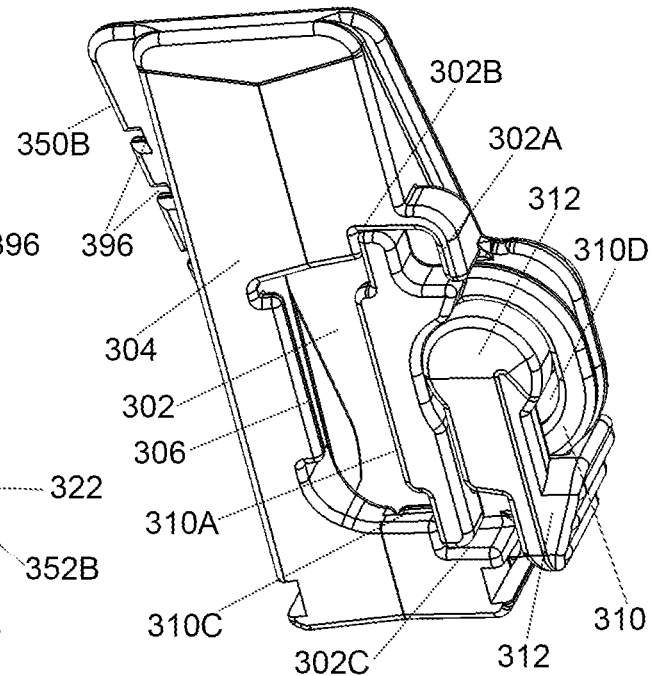

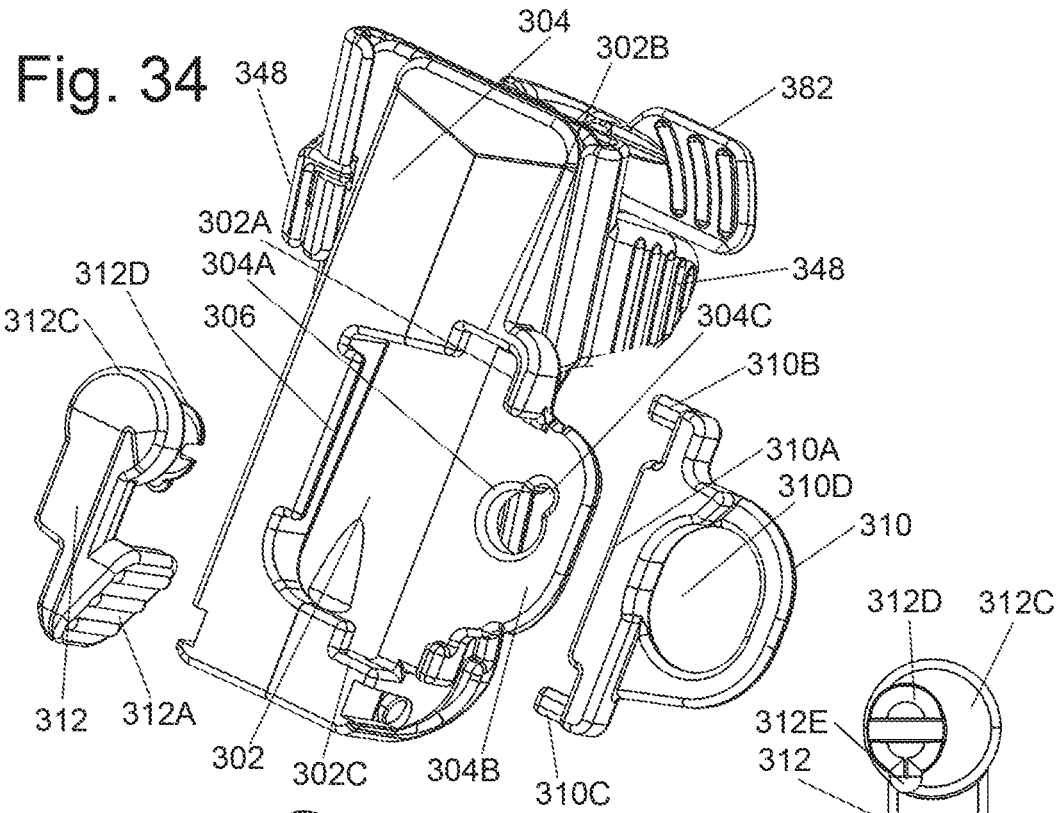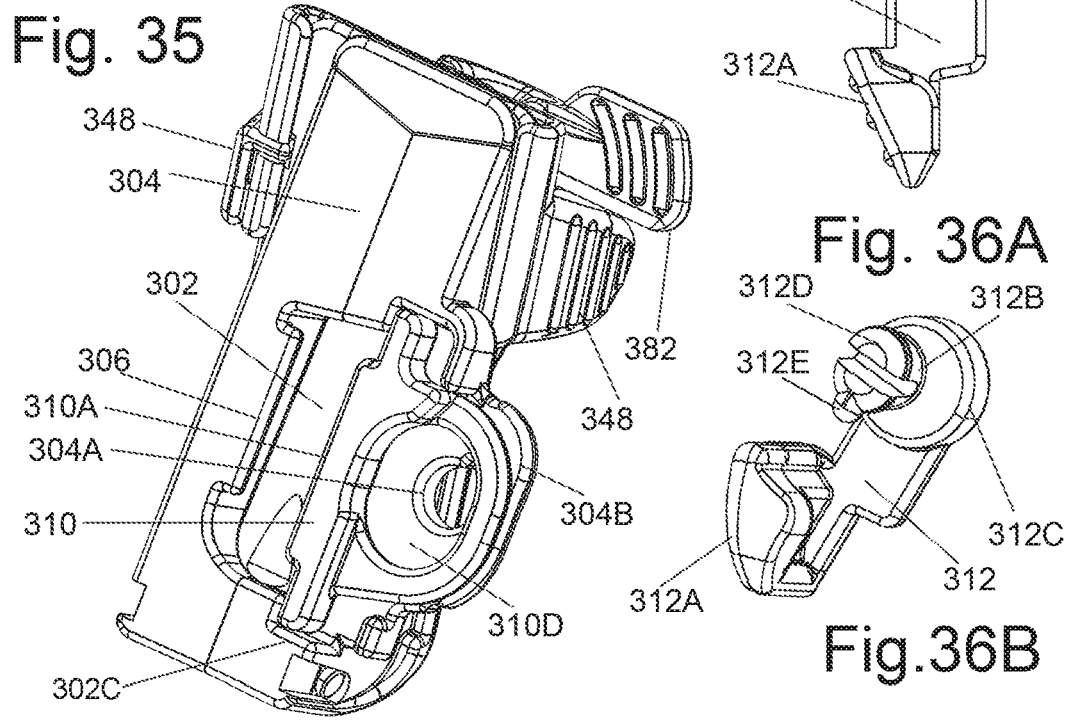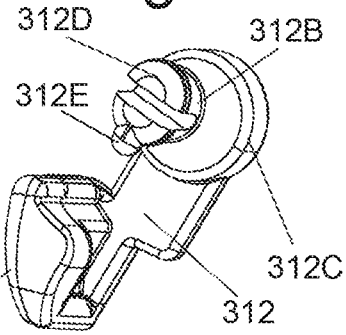

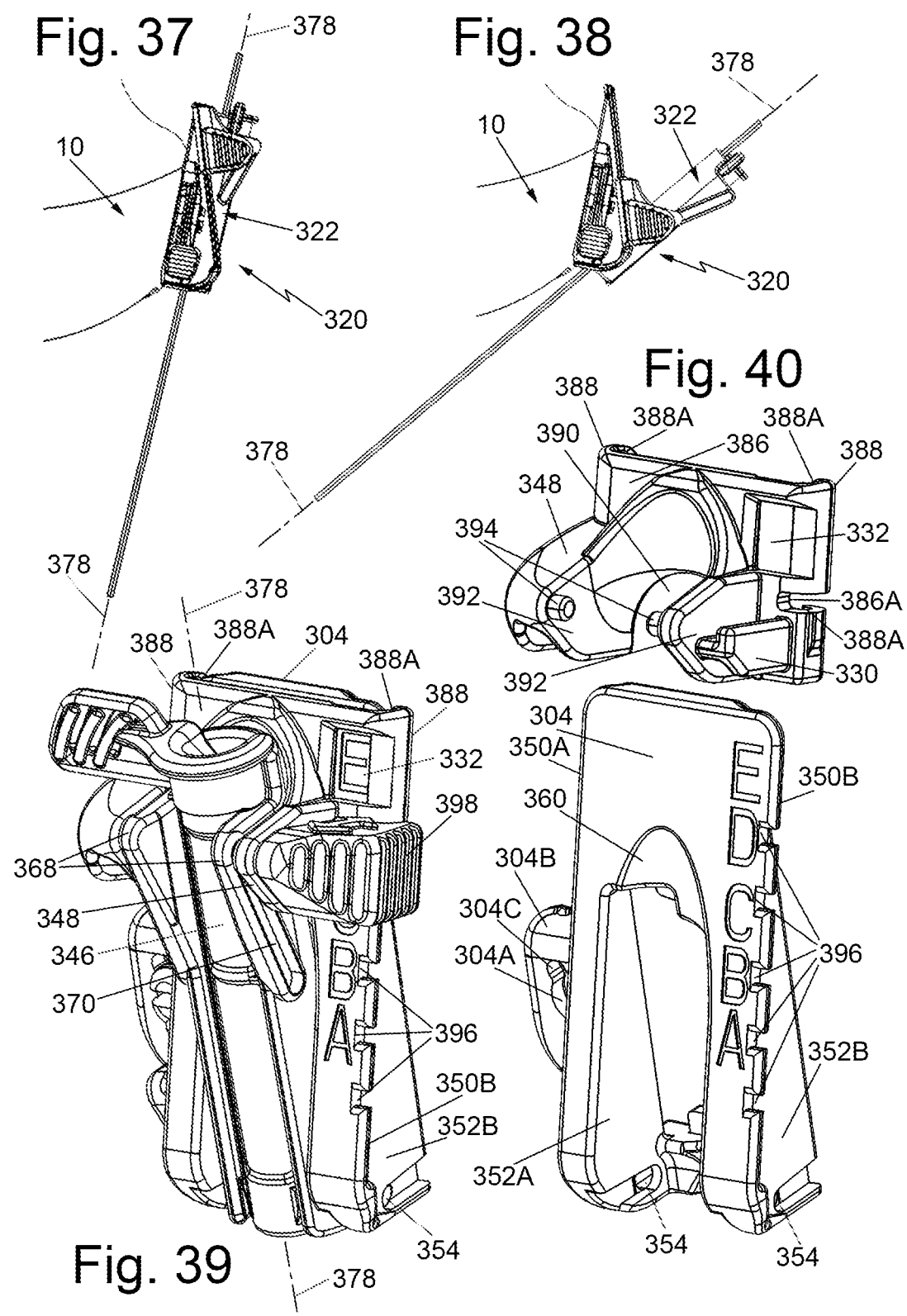

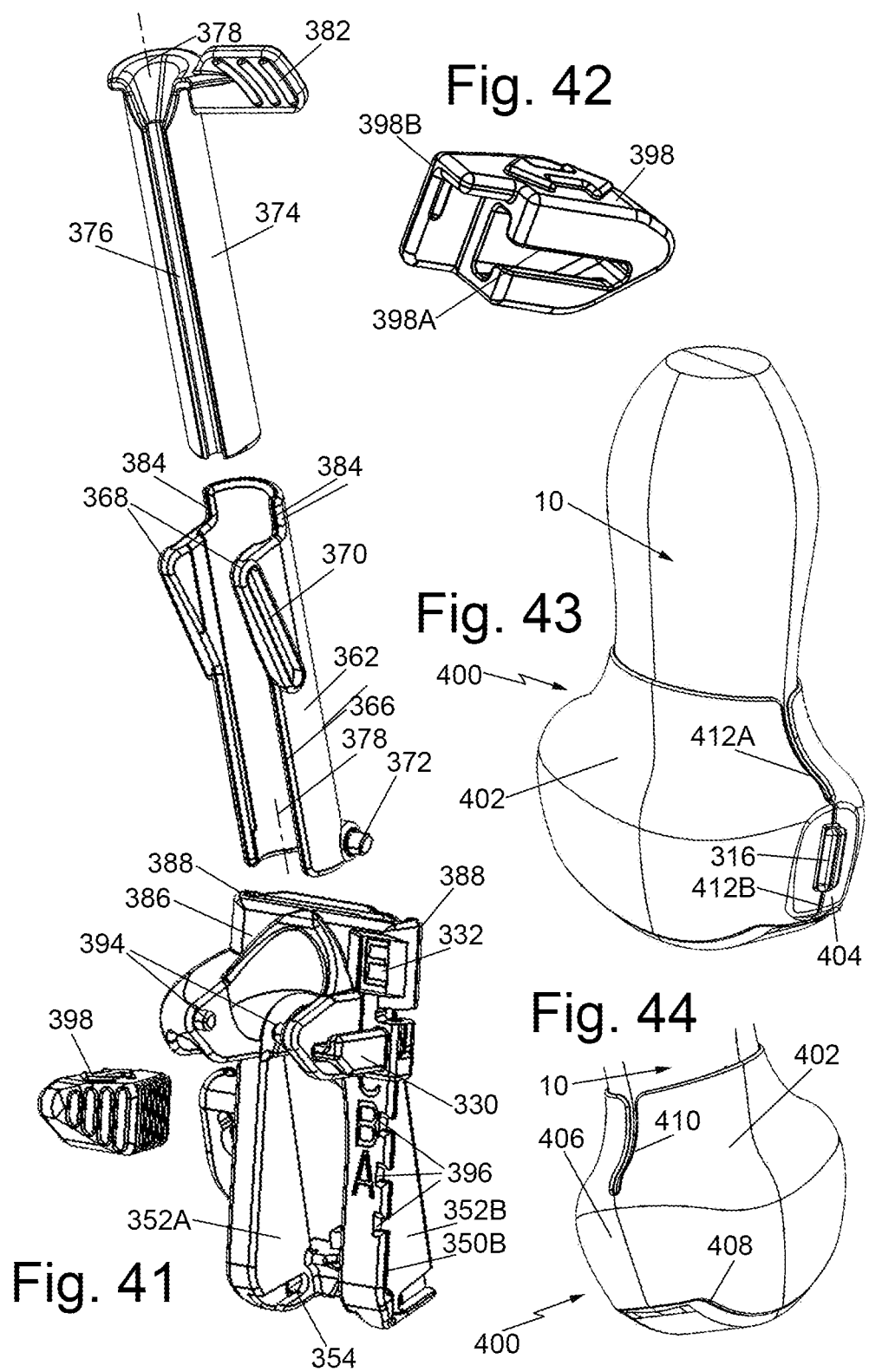

NEEDLE GUIDE DEVICES FOR MOUNTING ON IMAGING TRANSDUCERS OR ADAPTORS ON IMAGING TRANSDUCER, IMAGING TRANSDUCERS FOR MOUNTING NEEDLE GUIDE DEVICES AND ADAPTORS FOR IMAGING TRANSDUCERS FOR MOUNTING NEEDLE GUIDE DEVICES THEREON

CROSS-REFERENCE TO RELATED APPLICATIONS

This application claims priority under 35 U.S.C. § 119(e) from U.S. Provisional Application Ser. No. 62/078,744, filed on Nov. 12, 2014, entitled Needle Guide Devices For Mounting On Imaging Transducers Or Adaptors On Imaging Transducer, Imaging Transducers For Mounting Needle Guide Devices And Adaptors for Imaging Transducers for Mounting Needle Guide Devices Thereon, and also claims priority under 35 U.S.C. § 119(e) from U.S. Provisional Application Ser. No. 62/160,776, filed on May 13, 2015, entitled Needle Guide Devices For Mounting On Imaging Transducers Or Adaptors On Imaging Transducer, Imaging Transducers For Mounting Needle Guide Devices And Adaptors for Imaging Transducers for Mounting Needle Guide Devices Thereon, both of which applications are assigned to the same assignee as this application and whose disclosures are incorporated by reference herein.

FIELD OF THE INVENTION

This invention relates generally to needle guides for medical imaging instruments and more particularly to devices for guiding needles into selected locations of a patient relative to a medical instrument imaging sensor.

SPECIFICATION

Background of the Invention

Imaging instruments, such as ultrasound probes, have revolutionized the manner in which many important medical procedures are performed. These medical instruments utilize substantially non-invasive imaging techniques to explore and assess the condition of human tissue. As a result of these non-invasive imaging techniques, diagnostic and therapeutic protocols have been developed that allow many highly successful and safe procedures to be performed with a minimum of disturbance to patients. For example, ultrasound probes have become an accepted modality for exploring endocavities, e.g., the human digestive and reproductive tracts, of humans and animals in order to conduct routine examinations, as well as to identify evidence of tumors. In particular, using ultrasound, these tumors can be located and assessed. In conjunction therewith it is frequently desirable and even essential that biopsy samples of the tissue or fluid of a suspected tumor be removed for analysis. To that end, biopsy samples may be taken by carefully directing a hand-held needle, such as a biopsy instrument, catheter, or other thin instrument (hereafter referred to collectively as "needle" or "needles") into the body of a patient in order to remove a tissue sample. It is normally desirable that the needle be guided to a specific position within the body. Unfortunately, hand-held direction of a needle is often inadequate, being both inaccurate and time consuming. Thus, various needle guide devices have been designed for use with ultrasonic probes or other imaging transducers to assist in directing needles during imaging analysis.

Examples of such devices are found in the following United States Publications and Patents: 2006/0129046 (Stevens et al.), 2007/0049822 (Bunce et al.), 2012/0165679 (Orome et al.), Des. U.S. Pat. No. 424,693 (Pruter), U.S. Pat. No. 4,469,106 (Harui), U.S. Pat. No. 4,576,175 (Epstein), No. 4,899,756 (Sonek), U.S. Pat. No. 5,052,396 (Wedel et al.), U.S. Pat. No. 5,076,279 (Arenson et al.), U.S. Pat. No. 5,235,987 (Wolfe), U.S. Pat. No. 5,623,931 (Wung et al.), U.S. Pat. No. 5,758,650 (Miller et al.), U.S. Pat. No. 5,924,992 (Park et al.), U.S. Pat. No. 5,941,889 (Cermak), U.S. Pat. No. 6,203,499 (Imling et al.), U.S. Pat. No. 6,292,614 (Pruter), U.S. Pat. No. 6,361,499 (Bates et al.), U.S. Pat. No. 6,368,280 (Cermak et al.), U.S. Pat. No. 6,379,307 (Filly et al.), U.S. Pat. No. 6,485,426 (Sandhu), U.S. Pat. No. 6,884,219 (Pruter), U.S. Pat. No. 7,022,082 (Sonek), U.S. Pat. No. 7,087,024 (Pruter), U.S. Pat. No. 7,351,205 (Szczech et al.), U.S. Pat. No. 7,452,331 (Pruter), U.S. Pat. No. 7,588,541 (Floyd et al.), U.S. Pat. No. 7,635,336 (Pruter), U.S. Pat. No. 7,691,066 (Kosaku), U.S. Pat. No. 7,909,815 (Whitmore, III et al.) U.S. Pat. No. 7,926,776 (Cermak), U.S. Pat. No. 7,959,573 (Furia), U.S. Pat. No. 8,073,529 (Cermak et al.), U.S. Pat. No. 8,137,281 (Huang et al.), U.S. Pat. No. 8,216,149 (Oonuki et al.), U.S. Pat. No. 8,401,617 (Whitmore, III et al.) and U.S. Pat. No. 8,430,889 (Zeng et al.).

Some of the needle guides disclosed in the aforementioned patents and some commercially available needle guides are designed to be mounted on an ultrasonic probe or other imaging instrument that is itself enclosed within a sterile cover, such as a film. These covers serve to maintain the ultrasound sensor in a sterile environment, while reducing the likelihood of contamination between patients and also reduce the cost of medical procedures by minimizing sterilization costs.

Notwithstanding the existence of the many prior art needle guides currently available, a need exists for an improved needle guide that is disposable and can be securely mounted on a transducer with a cover and dismounted therefrom and without breaching or otherwise degrading the transducer's cover's integrity, with both of such actions being accomplished easily with minimal effort. A need also exists for a needle guide making use of a universal releasably securable locking feature to either facilitate its direct releasable attachment to prior art transducers by modifying their housings to include a common or universal transducer locating feature or coupling to which the universal releasably locking feature can be releasably secured or to facilitate the indirect releasable attachment of the needle guide to an unmodified prior art transducer by the use of a specially constructed bracket or adapter including a common or universal transducer locating feature to which the universal releasably locking feature can be releasably secured.

It is commonly a preference of users of ultrasound transducers on which a needle guide is mounted to be able to select a desired angled trajectory path to enable the user to reach an internal site in the patient's body that can be close to or far away from the transducer. That is typically achieved by using an adjustable angle needle guide or a fixed angle needle guide having a desired needle trajectory angle. When a prior art fixed angle needle guide is selected for the task of shallow needle penetration or a prior art adjustable needle guide is adjusted for a shallow needle penetration, the needle trajectory angle will be at a relatively large acute angle to the centerline of the transducer to bring the needle path close to transducer's image plane. In so doing, prior art needle guides typically have some portion which projects a substantial distance laterally outward from the transducer to establish that trajectory. That projecting portion creates a "blind" spot or zone by hiding or otherwise obscuring a portion of the patient's body from direct viewing by the user. Thus, a need also exists for a needle guide device that can establish a trajectory angle close to the image plane, without any portion of it projecting greatly outward laterally from the transducer to thereby minimize the size of any blind spot that could result. The subject invention also addresses that need.

Moreover, a need exists for an adjustable needle guide device that: (1) is configured to permit the user to change the trajectory angle trajectory of the needle after the needle guide has been mounted on the transducer and also to change the trajectory angle of the needle while the needle is disposed within the needle guide; (2) is configured to enable the user to select desired predetermined needle trajectory angles corresponding to guidelines overlaid on the ultrasound system; (3) permits the user to utilize a "free-hand" approach, i.e., to adjust the needle trajectory angle to any desired angle, to maintaining the needle within the ultrasound image plane of the transducer; and (4) is configured to enable the user to change the trajectory angle at any time, e.g., before introduction of the needle into the needle guide device or after the needle has been inserted therein. The subject invention also addresses those needs.

BRIEF SUMMARY OF THE INVENTION

In accordance with one aspect of this invention there is provided a needle guide device configured for releasable mounting on an imaging transducer or on an adaptor on an imaging transducer. The imaging transducer or the adaptor each includes a coupling member comprising a first portion. The needle guide device comprises a lockable mounting member and a needle guide assembly. The needle guide assembly comprises a body member and a needle holder. The needle holder is mounted on the body member and comprises an elongated passageway for receipt of a needle to establish the trajectory of the needle when the needle is located therein. The lockable mounting member comprises a slidable member having a second portion. One of the first portion and the second portion comprises a projection, and the other of the first portion and the second portion comprises a recess. The slidable member is configured to be slidably coupled to the body member and slidable from an unlocked position to a locked position and vice versa. The projection is configured for receipt in the recess to releasably secure the slidable member to the imaging transducer or the adaptor when the slidable member is in the locked position, thereby releasably mounting the needle guide device on the imaging transducer.

In accordance with another aspect of this invention the needle holder is adjustably mounted on the body member to enable the needle holder to be oriented to various selected orientations, e.g., from approximately 0° to approximately 40° degrees, with respect to the body member to establish various angled trajectories for the needle.

In accordance with another aspect of this invention the needle holder is oriented at a predetermined fixed angle with respect to the body member to establish a desired angled trajectory for the needle.

In accordance with another aspect of this invention, the slidable member comprises a portion of a lockable mounting assembly. The lockable mounting assembly comprises a body member including a stop. The stop is configured to engage the slidable member when the slidable member is in the locked position, whereupon the coupling member is held between the stop and the second portion of the slidable member.

In accordance with another aspect of this invention a needle guide device configured for mounting on an imaging transducer or on an adaptor on an imaging transducer is provided. The needle guide device comprises a base member, a barrel member, a slide member and a needle holder. The needle holder is mounted on the barrel member and comprises an elongated passageway for receipt of a needle to establish the trajectory of the needle when the needle is located therein. The barrel member is pivotably mounted on the base member. The slide member is slidable with respect to the base member and coupled to the barrel member to pivot the barrel member with respect to the base member to a first angular orientation when the slide member is slid to a first position, and to pivot the barrel portion with respect to the base member to a second angular orientation when the slide member is slid to a second position. The needle holder establishes a first angular trajectory for the needle when the barrel member is in the first angular orientation and establishes a second angular trajectory for the needle when the barrel member is in the second angular orientation. The second angular trajectory is different than the first angular trajectory.

In accordance with another aspect of this invention the needle guide assembly comprises a base member, a needle holder subassembly and a slide member. The needle holder subassembly comprises a barrel member and the needle holder. The needle holder is located in the barrel member and comprises an elongated passageway for receipt of a needle to establish the trajectory of the needle when the needle is located therein. The barrel member is pivotably mounted on the base member. The slide member is slidable with respect to the base member and coupled to the barrel member to pivot the barrel member with respect to the base member to a first angular orientation when the slide member is slid to a first position, and to pivot the barrel portion with respect to the base member to a second angular orientation when the slide member is slid to a second position. The needle holder establishes a first angular trajectory for the needle when the barrel member is in the first angular orientation and establishes a second angular trajectory for the needle when the barrel member is in the second angular orientation. The second angular trajectory is different than the first angular trajectory.

In accordance with another aspect of this invention the barrel member comprises a cylindrical cavity having a central longitudinal axis and wherein the needle holder comprises an elongated cylindrical member located within the cylindrical cavity and rotatable about the central longitudinal axis. The needle holder has a passageway extending therethrough parallel to the central longitudinal axis. The passageway is configured for receipt of the needle therein to establish the needle's trajectory. The barrel portion includes a slot in communication with the cylindrical cavity and extending parallel and to the central longitudinal axis. The needle holder comprises a slot in communication with the passageway. The needle holder is rotatable within the cylindrical cavity between a closed and open position, and vice versa. The slot in the needle holder is aligned with the slot in the barrel when the needle holder is rotated to the open position. When in the open position a needle extending through the passageway can be removed from the needle holder laterally through the aligned slots and a needle can be introduced into the passageway laterally through the aligned slots. The slots are unaligned when the needle holder is in the closed position, whereupon a needle disposed in the passageway is held therein.

In accordance another aspect of this invention the barrel member comprises a cylindrical cavity having a central longitudinal axis and wherein the needle holder comprises an elongated cylindrical member located within the cylindrical cavity and rotatable about the central longitudinal axis. The needle holder has a passageway extending therethrough parallel to the central longitudinal axis. The passageway is configured for receipt of the needle therein to establish the needle's trajectory. The barrel portion includes a slot in communication with the cylindrical cavity and extending parallel and to the central longitudinal axis. The needle holder comprises a slot in communication with the passageway. The needle holder is rotatable within the cylindrical cavity between a closed and open position, and vice versa. The slot in the needle holder is aligned with the slot in the barrel when the needle holder is rotated to the open position. When in the open position a needle extending through the passageway can be removed from the needle holder laterally through the aligned slots and a needle can be introduced into the passageway laterally through the aligned slots. The slots are unaligned when the needle holder is in the closed position, whereupon a needle disposed in the passageway is held therein.

In accordance with another aspect of this invention there is provided an imaging transducer for providing a signal representing an image of an internal portion of the body of a patient for visualization by a user of the imaging transducer. The imaging transducer has a housing comprising a coupling member for enabling the releasable securement of a needle guide device thereto. The needle guide device comprises a lockable mounting member having a second portion. The coupling member comprises a first portion. One of the first portion and the second portion comprises a projection, and the other of the first portion and the second portion comprises a recess. The lockable mounting member is slidable from an unlocked position to a locked position with respect to the needle guide device, and vice versa. The projection is configured for receipt in the recess to releasably secure the lockable mounting member to the coupling member when the lockable mounting member is in the locked position, thereby releasably mounting the needle guide device on the imaging transducer.

In accordance with another aspect of this invention there is provided an adaptor for mounting on an imaging transducer. The imaging transducer is configured for providing a signal representing an image of an internal portion of the body of a patient for visualization by a user of the imaging transducer. The adaptor has a housing comprising a coupling member for enabling the releasable securement of a needle guide device thereto. The needle guide device comprises a lockable mounting member. The lockable mounting member has a second portion. The coupling member comprises a first portion. One of the first portion and the second portion comprises a projection, and the other of the first portion and the second portion comprises a recess. The lockable mounting member is slidable from an unlocked position to a locked position with respect to the needle guide device, and vice versa. The projection is configured for receipt in the recess to releasably secure the lockable mounting member to the coupling member when the lockable mounting member is in the locked position, thereby releasably mounting the needle guide device on the adaptor.

BRIEF DESCRIPTION OF SEVERAL VIEWS OF THE DRAWINGS

FIG. 1 is an isometric view of one exemplary embodiment of a needle guide device constructed in accordance with this invention shown mounted on an imaging transducer, e.g., an ultrasound probe, with a conventional cover interposed therebetween, and with the needle guide device being configured to provide a needle trajectory angle that can be varied as desired;

FIG. 2 is an enlarged isometric view of the needle guide device shown in FIG. 1, but without the needle shown therein;

FIG. 3 is an isometric view of the bottom portion of the imaging transducer of FIG. 1 showing a coupling member serving as a locating feature for releasably mounting the needle guide on the transducer;

FIG. 4 is a top plan view of the coupling member of the imaging transducer shown in FIG. 3;

FIG. 5 is an enlarged isometric view of a lockable mounting member forming a portion of the needle guide device of FIGS. 1 and 2 shown adjacent the coupling member of the imaging transducer, to enable the lockable mounting member to be releasably secured thereto to releasably mount the needle guide device on the transducer;

FIG. 13 is an isometric view of the needle guide device of FIGS. 1 and 2 shown mounted on an adaptor bracket constructed in accordance with one aspect of this invention, with the adaptor bracket being mounted on a conventional imaging transducer, e.g., an ultrasound probe, with a conventional cover interposed therebetween (although not shown in this figure);

FIG. 14 is an isometric view of the adaptor bracket of FIG. 13 shown mounted on a conventional imaging transducer;

FIG. 15 is an enlarged isometric view of the bottom portion of the adaptor bracket of FIG. 14 showing a coupling member thereof which serves as a locating feature for releasably mounting the needle guide device on the adaptor bracket and hence on the conventional imaging transducer;

FIG. 16 is a top elevation view of the portion of the coupling member of the adaptor bracket shown in FIGS. 14 and 15;

FIG. 17 is a reduced isometric view of the adaptor bracket of FIG. 14 but showing the opposite side thereof, i.e., the side opposite the coupling member;

FIG. 22 is an exploded isometric view of the needle guide assembly shown in FIG. 18 taken from a front oblique angle;

FIG. 23 is an exploded isometric view of the needle guide assembly shown in FIG. 18 taken from the rear side thereof;

FIG. 24 is an isometric view of the needle guide device of FIG. 18, but with a component thereof in an open position to enable a needle to be inserted laterally into the needle guide device or removed laterally from the needle guide device;

FIG. 25 is an isometric view of an adaptor bracket constructed in accordance with this invention shown mounted on a conventional transducer, e.g., an ultrasound probe, to enable a needle guide device like shown in FIG. 18 to be mounted thereon;

FIG. 26 is an isometric view of one exemplary embodiment of a needle guide device constructed in accordance with this invention shown mounted on an imaging transducer, e.g., an ultrasound probe, and with the needle guide device being configured to provide a needle trajectory angle that can be varied as desired, but which as shown has been adjusted to establish a 3° angle of penetration the needle;

FIG. 27 is an isometric view similar to FIG. 26, but showing the needle guide device adjusted to establish a 40° angle of penetration for the needle;

FIG. 28 is a slightly enlarged isometric view of the bottom portion of the imaging transducer of FIG. 26 showing a coupling member serving as a locating feature for releasably mounting the needle guide device on the transducer;

FIG. 29 is a top plan view of the coupling member of the imaging transducer taken along line 29-29 of FIG. 28;

FIG. 30 is a front elevation view of the coupling member shown in FIGS. 28 and 29;

FIG. 31 is an enlarged front oblique isometric view showing the needle guide device of FIG. 26 about to be mounted on the imaging transducer via the coupling member shown in FIGS. 28-30;

FIG. 32 is an front oblique isometric view of a portion of the needle guide device of FIG. 31 for releasable securement to the coupling member shown in FIGS. 26-28 to releasably mount the needle guide device onto the imaging transducer;

FIG. 33 is a rear oblique isometric view of the portion of the needle guide device shown in FIG. 32;

FIG. 34 is an enlarged exploded isometric view showing a portion of a lockable mounting assembly forming a portion of the needle guide device of FIG. 26;

FIG. 35 is an isometric view similar to FIG. 34 but showing the lockable mounting member of the lockable mounting assembly disposed within a corresponding slot in the body member of the needle guide device;

FIG. 36A is a slightly enlarged elevation view of the locking lever forming a portion of the lockable mounting assembly shown in FIG. 34;

FIG. 36B is an isometric view of the locking lever shown in FIG. 36A;

FIG. 37 is a reduced side elevation view of the needle guide device shown in FIG. 26;

FIG. 38 is a reduced side elevation view of the needle guide device shown in FIG. 27;

FIG. 39 is an enlarged front oblique isometric view of the needle guide device shown in FIG. 31 but taken from a different angle to more clearly show the mechanism for adjusting the angle of penetration for a needle located within the needle guide device;

FIG. 40 is an exploded isometric view showing a portion of the mechanism for adjusting the angle of penetration for a needle located within the needle guide device;

FIG. 41 is an exploded isometric view of the needle guide device of FIG. 26, but without the lockable mounting assembly;

FIG. 42 is an enlarged isometric view of a lock slide or lever forming a portion of the mechanism for adjusting the angle of penetration of a needle located within the needle guide device;

FIG. 43 is a reduced isometric view of an adaptor constructed in accordance with one aspect of this invention shown mounted on a conventional imaging transducer to enable a needle guide device constructed in accordance with this invention to be able to be mounted thereon, and hence mounted on a conventional imaging transducer; and FIG. 44 is an isometric view similar to FIG. 43, but showing the opposite side of the adaptor, i.e., the side opposite the coupling member, mounted on the conventional imaging transducer shown in FIG. 43.

DETAILED DESCRIPTION OF PREFERRED EMBODIMENTS

Figure 18:
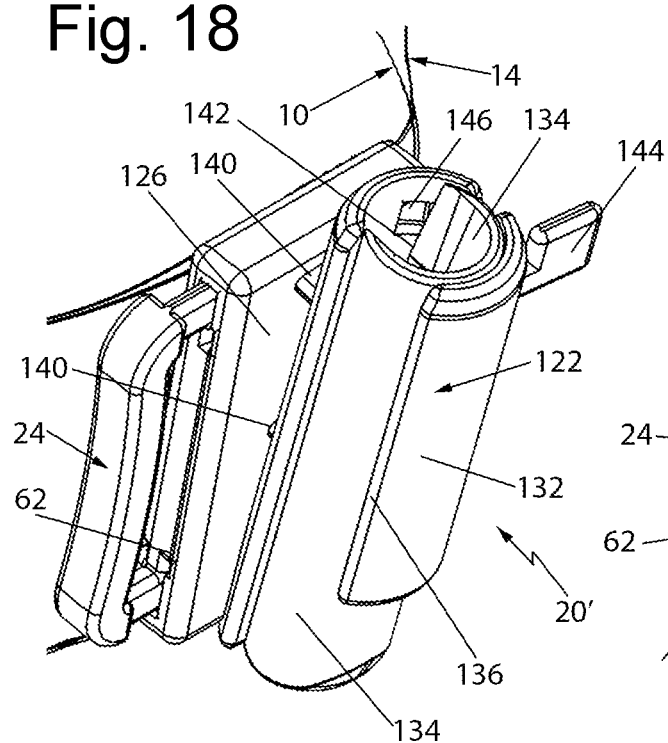
FIG. 18 is an isometric view of another exemplary embodiment of a needle guide device constructed in accordance with this invention shown mounted on an imaging transducer, e.g., an ultrasound probe, with a conventional cover interposed therebetween, and with the needle guide device being configured to provide a fixed predetermined needle trajectory angle.
Figure 19:
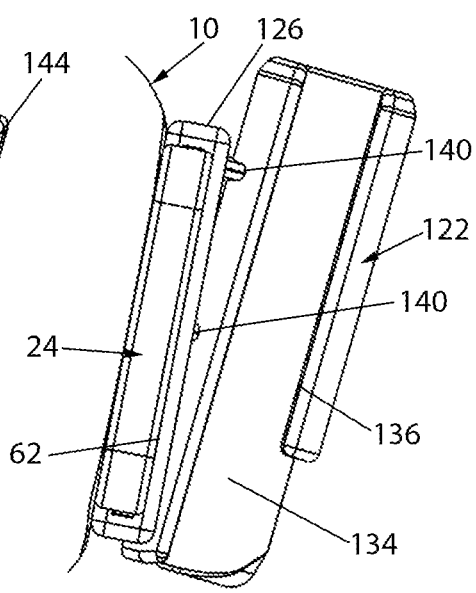
FIG. 19 is a side elevation view of the needle guide shown in FIG. 18.
Figure 21:
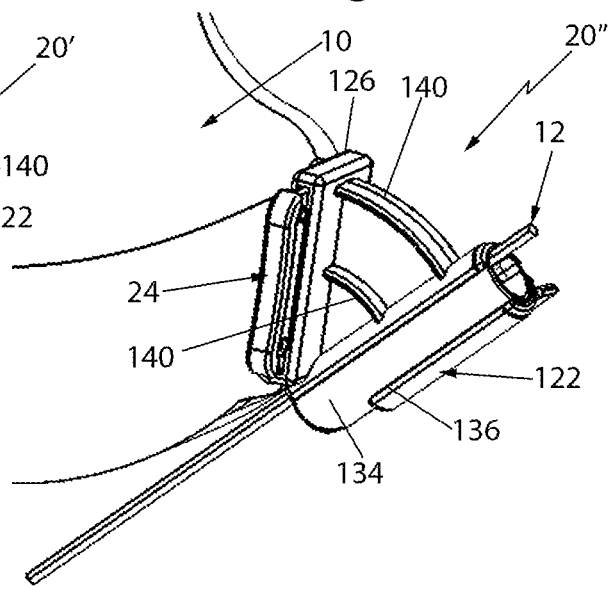
FIG. 21 is a side elevation view, similar to that of FIG. 20, but showing the needle guide device of FIG. 18 establishing a 40° angle trajectory for the needle.

Referring now to the various figures of the drawing wherein like reference characters refer to like parts, there is shown in FIG. 1 one exemplary preferred embodiment of a reusable needle guide device 20 constructed in accordance with this invention. Another preferred exemplary embodiment of a reusable needle guide device 20' constructed in accordance with this invention is shown in FIG. 18. Still another reusable needle guide device 20" constructed in accordance with this invention is shown in FIG. 21. Those three exemplary embodiments are configured to be releasably mounted directly on an imaging instrument, e.g., an ultrasound transducer or probe 10, or indirectly mounted on an adaptor bracket 200 constructed in accordance with this invention and shown in FIGS. 13 and 25, to guide a needle 12 or any other elongated instrument through a desired path or trajectory into the body of a patient (human or animal) for a tissue biopsy procedure or any number of other medical procedures.

As will be seen and described in detail later the needle guide device 20 is adjustable, so that it can establish a trajectory path enabling the needle or instrument to reach an internal site in the patient's body that is close to or far away from the distal or working end of the transducer. In particular, the needle guide device 20 is configured to enable the user to adjust the needle angle trajectory through a wide range, e.g., a range of approximately 40 degrees. The needle guide device 20' of FIG. 18 and the needle guide device 20" of FIG. 21 are not adjustable. Rather, each establishes a fixed, different respective, trajectory angle for the needle or other instrument. In accordance with one preferred aspect of this invention a plurality of fixed angle needle guide devices, like guides 20' and 20" can be provided in the form of a kit of several fixed needle guide devices, each establishing its own, and different, angled trajectory path. Thus, by the appropriate selection of the fixed angle needle guide the user can establish the desired angular path for the needle or other instrument.

Irrespective of whether the needle guide device is an adjustable angle or fixed angle device, all of the needle guide devices of this invention make use of a mounting feature to enable them to be readily and quickly mounted on an imaging transducer 10, with a conventional cover 14 interposed therebetween. That cover is typically formed of a thin, flexible sheath of any suitable material, e.g., latex, into a suitable shape, e.g., condom-shaped sheath, to be placed over the imaging transducer before the needle guide device is mounted thereon to keep the transducer sanitary. In the interest of drawing simplicity the cover has been omitted from many of the figures of the drawing, it being understood that the cover is, in fact, interposed between the needle guide device and the imaging transducer on which the needle guide device is mounted or interposed between the needle guide device and the adaptor bracket on which the needle guide is mounted.

The releasably mounting feature of this invention will be described in detail later. Suffice it for now to state that the exemplary needle guide devices 20, 20' and 20" include a locking member that is configured to be slidably releasably secured to a locating feature or coupling member that is provided on a specially constructed imaging transducer housing or is provided on a bracket or adapter for use on a conventional imaging transducer. Moreover, the adjustable needle guide device 20 and the fixed needle guide device 20" (and all other needle guides constructed in accordance with subject invention), enable the user to establish a very shallow depth of penetration for a needle, with a minimal blind spot, since the needle guides do not include any portion which projects far out from the transducer to block the view of the user, i.e., all of the needle guide devices of this invention have a compact form factor.

Turning now to FIGS. 1 and 2 it can be seen that the needle guide device 20 basically comprises a needle guide assembly 22 and a lockable mounting member 24. The lockable mounting member is configured to be releasably secured to a universal or common locating feature or coupling member 16 that is located on the housing of the transducer adjacent the distal or working end of the transducer. The coupling member 16 is preferably mounted at the location of the typical "#1 array indicator" of a conventional ultrasonic transducer. As best seen in FIGS. 3-5 the coupling member 16 is in the form of a projection of somewhat rectangular profile and having an enlarged top portion 16A and a pair of undercut recesses 16B on the opposed long sides of the projection.

Figure 6:
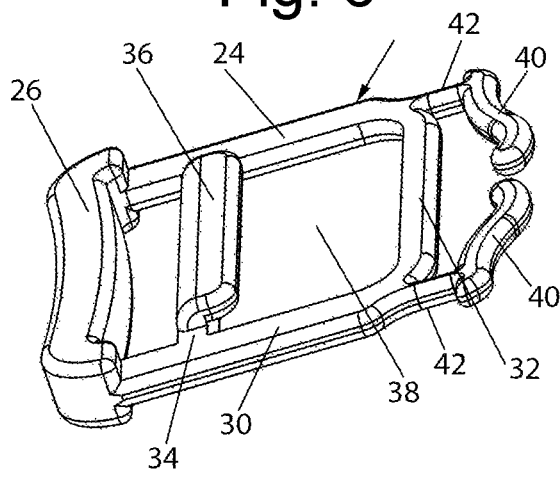
FIG. 6 is an isometric view of the lockable mounting member shown in FIG. 5.
Figure 7:
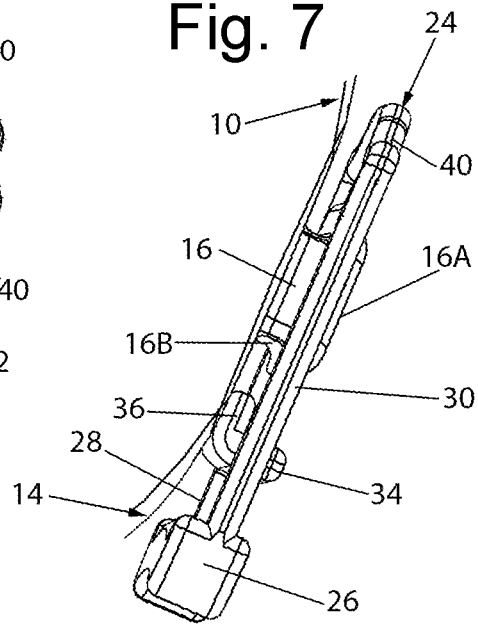
FIG. 7 is an isometric view of the lockable mounting member of FIG. 5, but taken from a different direction.

The lockable mounting member 24 is best seen in FIGS. 6 and 7 and basically comprises a rectangularly shaped frame, e.g., an integrally molded plastic component, having one side section in the form of a thickened handle 26, a pair of intermediate sections 28 and 30 extending from respective ends of the handle section and an opposite side section 32 connected between the intermediate sections. A crosspiece section 34 extends parallel and closely adjacent the handle section. The cross piece includes a projection, e.g., a flange, 36 extending along the length thereof. As best seen in FIG. 6, the sections 26, 28, 30 and 32 define a window 38 therebetween. The window 38 is configured to receive the transducer's coupling member 16 and the portion of the cover 14 overlying the top 16A of the coupling member when the guide device 20 is to be mounted on the transducer. In particular, as will be described in detail later, the lockable mounting member 24 is configured to be slidably received within a slot or channel 62 (to be described later) forming a portion of the needle guide assembly 22 so that it can be slid by a user pushing on the handle from an open position wherein the coupling member is located within the window 38, to a locked position, and vice versa. When the lockable mounting member is in the locked position the coupling member is still located within the window 38, but the flanged projection 36 is disposed within the confronting undercut recess 16B of the coupling member 16. This action releasable secures the lockable mounting member 24 to the transducer coupling member.

In order to ensure that the lockable mounting member is held in the locked position so that it is resistant to accidental displacement, it includes a pair of extending fingers 40 projecting outward from the respective ends of its side section 32. Each finger 40 is connected to its respective end of the side section 32 by a short flexible bridge section 42, which engages a respective portion in the slot or channel 62 of the needle guide assembly to securely hold the lockable mounting member in the locked position. The bridge sections 42, being resilient, are effectively spring-biased so that they are configured to be flexed inward when the fingers 40 are squeezed together by a user. This brings the bridge sections 42 towards each other to thereby release the lockable mounting member 24 from its locked position. That action enables the lockable mounting member to be slid to its open position, wherein the flanged projection 36 is outside of (beyond) the undercut recess 16B of the coupling member and with the coupling member being within the window 38 to effectively free the coupling member, thereby disconnecting the needle guide device from the imaging transducer. If desired, the lockable mounting member can be removed from the needle guide by squeezing the fingers 40 together after the transducer's coupling member 16 is out of the window 38 and then pulling on the handle 36 to pull the lockable mounting member out of the slot or channel 62.

Figure 8:
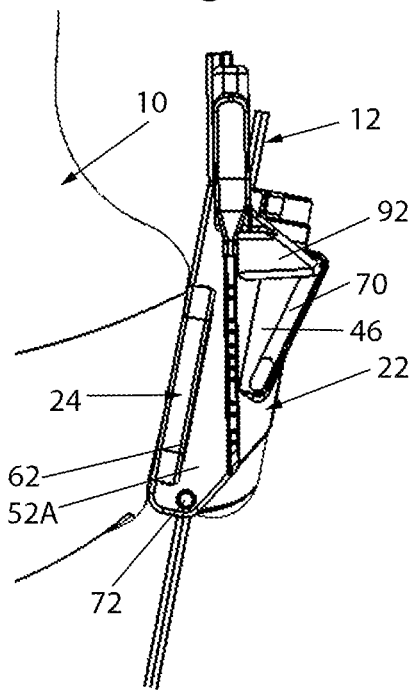
FIG. 8 is a reduced side elevation view of the needle guide device of FIG. 1 shown on the transducer establishing a 0° angle trajectory for the needle.
Figure 9:
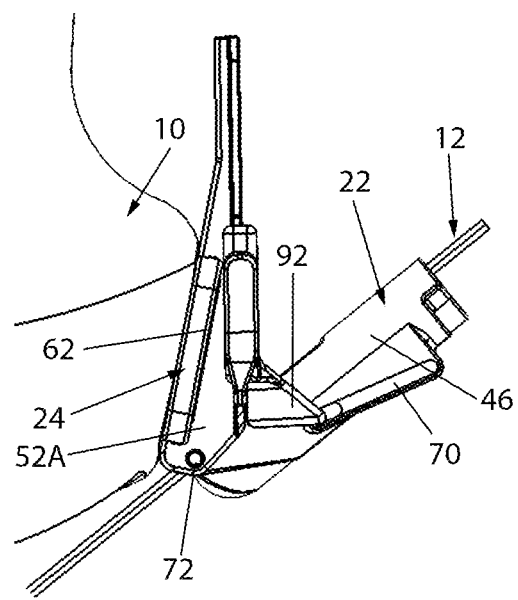
FIG. 9 is a side elevation view, similar to that of FIG. 8, but showing the needle guide device of FIG. 1 establishing a 40° angle trajectory for the needle.
Figure 10:
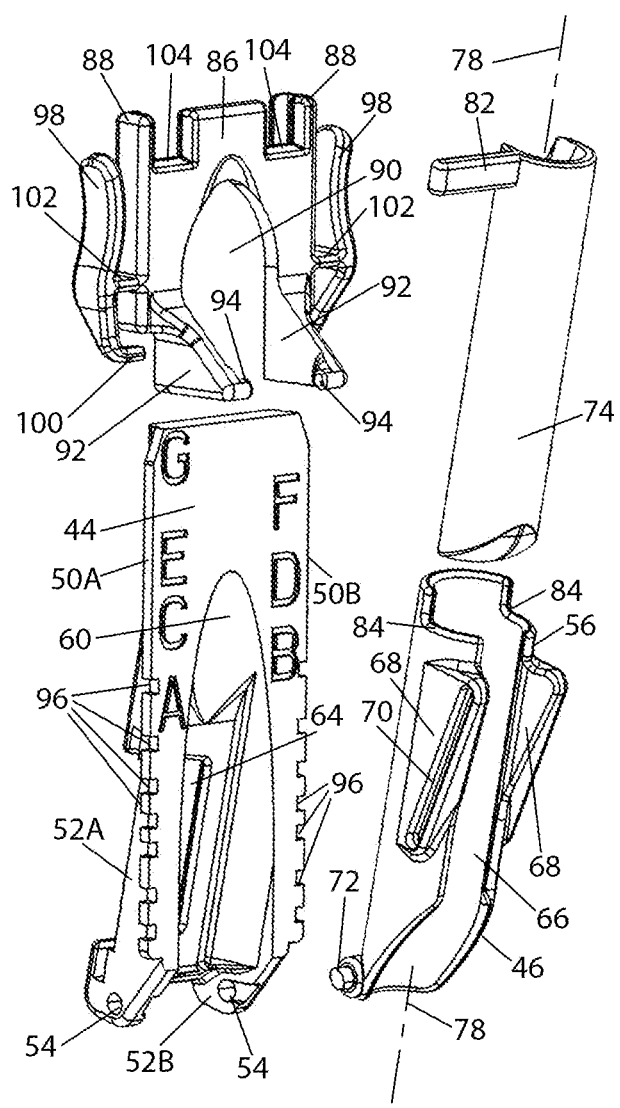
FIG. 10 is an exploded isometric view of the needle guide assembly shown in FIG. 2 taken from a front oblique angle.
Figure 11:
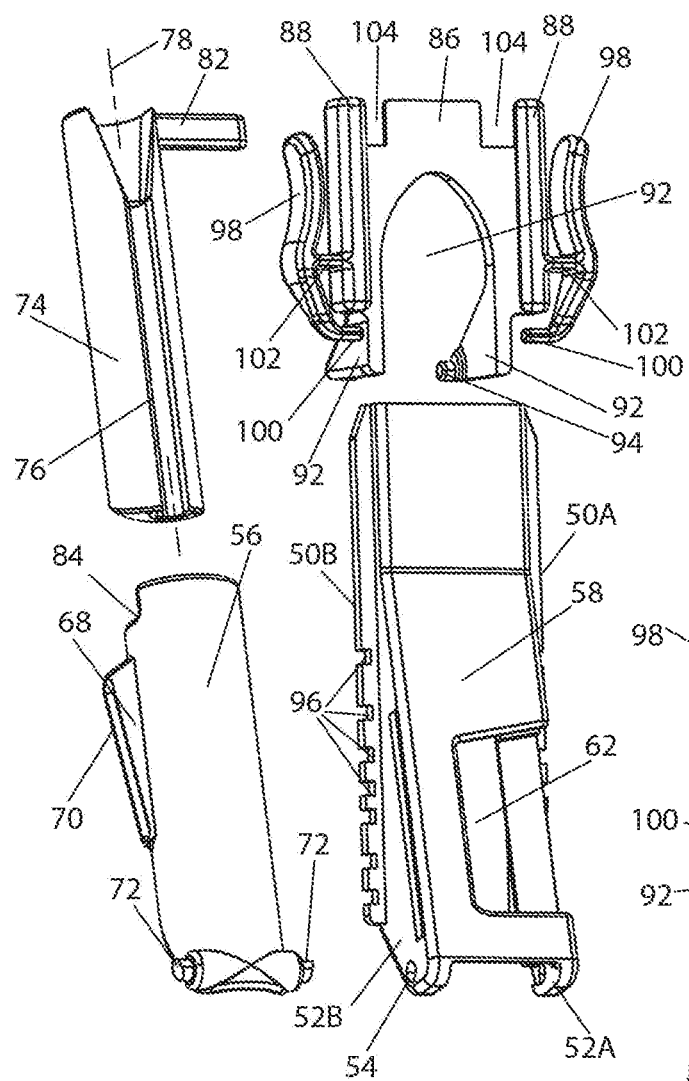
FIG. 11 is an exploded isometric view of the needle guide assembly shown in FIG. 2 taken from a rear oblique angle.

Referring now to FIGS. 2, 10 and 11 the details of the needle guide assembly 22 will now be described. To that end, it basically comprises a body or base member 44, a needle holder subassembly 46 and a slide member 48. Each is molded of a suitable plastic material. The body member 44 comprises a generally flat panel having a pair of long sides 50A and 50B. A pair of triangularly shaped flanged ears 52A and 52B project rearwardly from the bottom portions of the sides 50A and 50B, respectively. Each ear includes a short slot terminating in a circular hole 54 for accommodating a respective pivot pin of a cylindrically shaped barrel member 56 (to be described shortly) forming a portion of the needle holder subassembly 46. The holes 54 are axially aligned. A generally planar back wall 58 extends between the marginal edges of the triangular ears as best seen in FIG. 9. The front portion of the body member 44 includes an arcuate recess or cavity 60, as best seen in FIG. 8, which is configured to accommodate the barrel member 56. The back wall 58 includes a slot or channel 62 extending from one side of the back wall to the other and is open to the back surface of the back wall from the ear 52A to a point adjacent the ear 52B. A central opening 64 is located in the front surface of the back wall and is shaped to accommodate the top portion 16A of the transducer coupling member 16 to releasably secure the needle guide device to the transducer.

The barrel member 56 is an elongated generally tubular member having a centrally located front slot 66 extending parallel to the central longitudinal axis 78 of the barrel member. A pair of triangular ears 68 project outward from the barrel member 56 on opposite sides of the slot 66. Each ear includes a linear slot or track 70 (only one of which can be seen in the figures) which extends at an acute angle, e.g., 15°, from the longitudinal axis of the barrel member, and oriented upward and outward as shown in FIGS. 2 and 8-12. The bottom edge portion of the barrel member includes a pair of pivot pins 72 projecting outward therefrom. The pins 72 are diametrically opposed and axially aligned, and each pin is configured to be disposed within a respective hole 54 in the body member 44. When so located the barrel member is able to pivot with respect to the body member about the axis of the aligned holes and pins to enable the barrel to assume any desired angular position with respect to the body member from 0° (as shown in FIG. 8) to 40° (as shown in FIG. 9). The means for effecting the pivoting of the barrel member with respect to the base member is the heretofore identified slide member 48.

Figure 12:
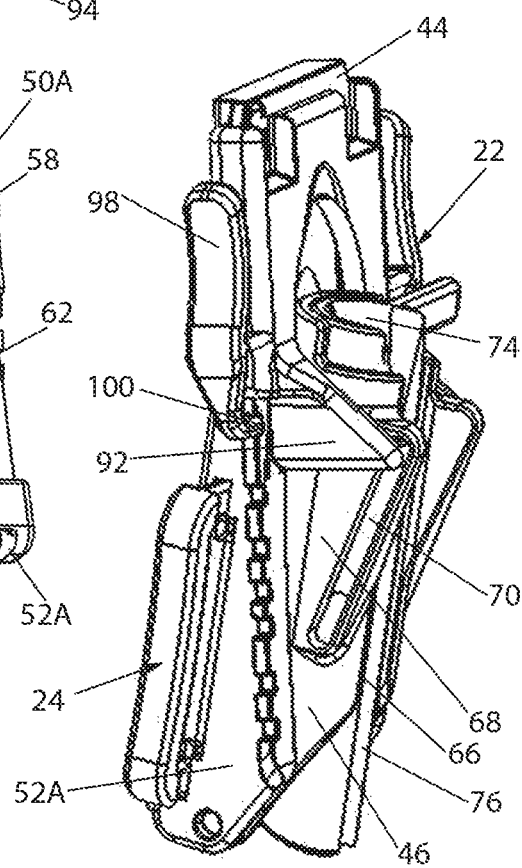
FIG. 12 is an isometric view of the needle guide device, like that shown in FIG. 2, but with a component thereof in an open position to enable a needle to be inserted laterally into the needle guide device or removed laterally from the needle guide device.

Before describing the slide member, a description of the member for holding the needle 12 in the needle guide device 20 is in order. That member is best seen in FIGS. 10 and 11. It is in the form of an elongated cylindrical needle holder or insert 74. The insert is molded of any suitable plastic material and is configured to be disposed within the barrel member 46 to directly hold the needle 12 therein. Moreover, as will be seen and described later, the insert 74 is configured to be rotated about the central axis 78 of the barrel member between an open position, such as shown in FIG. 12, and a closed position, such as shown in FIG. 2, and vice versa. The insert 74 has a slot 76 extending parallel to the central longitudinal axis 78 of the insert from one end of the insert to the other. The width of the slot 76 is just slightly larger than the diameter of the particular diameter needle 12 to be used with the needle guide device. The inner end 80 of the slot 76 extends parallel to the central longitudinal axis 78 and is circular in shape to accommodate the needle 12 therein. The depth of the slot, i.e., the distance from the outer surface of the insert (and the inner surface of the barrel member) to the inner end of the slot is just slightly larger than the diameter of the needle. Thus, when the needle is inserted in the slot 76 a portion of the periphery of the slot at the inner end 80 engages the needle, while a portion of the inner surface of the barrel member contiguous with the slot engages another portion of the periphery of the needle, thereby holding the needle in place along a path that is parallel to the longitudinal central axis 78 of the needle holder. That path establishes the trajectory for the needle.

It should be pointed out at this juncture that different inserts with different size slots 76 can be provided in lieu of the insert 76 shown herein to accommodate different diameter needles.

As best seen in FIG. 11 the upper or entrance end of the slot 76 is chamfered or tapered to facilitate the axial introduction of the needle therein, i.e., the tapered or chamfered surface directs the distal end of the needle towards the slot when the needle is introduced axially.

A tab 82 projects radially outward from the top end of the insert to enable the user to rotate the insert 76 about central longitudinal axis 78 within the barrel member between the open and closed positions. In order to accommodate the tab 82 the upper end of the barrel member has a pair of notches 84 immediately adjacent each side of the slot 66. The ends of the notches establish a pair of stops enabling the insert to be rotated through an angle of 180 degrees and no more.

When the needle holder or insert 74 is in the open position, like that shown in FIG. 12, the needle 12 can be inserted laterally therein, instead of axially through the chamfered upper end of the insert as discussed above. To that end, the tab 82 is grasped by the user to rotate the insert 74 180° about central longitudinal axis 78 (which is also the longitudinal central axis of the barrel member) from the position shown in FIGS. 1 and 2 to the position like shown in FIG. 12. At that time the slot 76 of the insert will be aligned with the slot 66 of the barrel member, whereupon the needle can be inserted laterally through the aligned slots. Once the needle is in the slot 76 and parallel to the longitudinal central axis 78, the tab 82 can be rotated 180° back to the closed position shown in FIGS. 1 and 2, thereby holding the needle in place.

As will be appreciated by one skilled in the art, after the needle has been deployed, i.e., inserted into the patient's body along the desired trajectory, the imaging transducer 10 and needle guide device 20 can be freed (removed) from the needle leaving the needle 12 in place by merely rotating the insert 74 to its open position, like shown in FIG. 12, whereupon the imaging transducer 10 and needle guide device 20 mounted thereon can be moved as a unit laterally with respect to the needle 12 so that the needle passes through the aligned slots 66 and 77.

Turning now to FIGS. 10 and 11 the details of the construction and operation of the slide member 48 will be described. The slide member basically comprises a generally planar body section 86 having a thickened pair of side flanges 88, each of which includes a longitudinally extending slot or channel for receipt of a respective side edge 50A or 50B of the base member 44 to slidably mount the slide member thereon. The central portion of the body section includes a recess or cavity 90 to accommodate the barrel member 46 when it is in its 0° orientation, i.e., when the slot 76 of the needle holder mounted within the barrel member extends parallel to the plane of the slot 62 of the base member. That orientation is shown in FIGS. 1 and 8. A pair of ears 92 project outward perpendicularly from the bottom of the body section 86 on each side of the slot 90. Each ear terminates in a free end from which a pivot pin 94 projects. The pivot pins 94 are axially aligned and each is configured to be disposed within a respective one of the angularly extending tracks 70 of the barrel member.

When the slide member 48 is its upper-most position with respect to the base member 46, the pivot pins 94 of the slide member will be at the upper ends of the tracks 70 of the barrel member, whereupon the barrel member will be pivoted about its pivot pins 70 to the 0° angular orientation shown in FIG. 8. Conversely, when the slide member 48 is its lower-most position with respect to the base member 46, the pivot pins 94 of the slide member will be at the lower ends of the tracks 70 of the barrel member, whereupon the barrel member will be pivoted about its pivot pins 70 to the 40° angular orientation shown in FIG. 9.

The exemplary embodiment of the variable angle needle guide device 20 shown herein includes a detent mechanism to hold the barrel member in any one of a number, e.g., seven, discrete distinct predetermined angular orientations with respect to the base member, so that the slide member can be readily and repeatedly slid to any one of those positions and to be held therein against accidental displacement therefrom. The detent mechanism basically comprises a plurality of pairs of notches 96 (FIGS. 10 and 11) extending along the sides 50A and 50B of the base member at various predetermined spaced locations therealong and which are configured to be engaged by pair of fingers on the slide member to releasably hold the slide member at the position established by the pair of notches into which the fingers have been disposed. Thus, as can be seen, the slide member 48 includes a pair of pivotable arms 98 mounted on the side flanges 88. The upper end of each arm 98 is in the form of a handle and a lower portion in the form of an inwardly directed free end finger 100. Each arm is mounted on a respective one of the side flanges by a flexible bridge section 102, whereupon when the handles 98 are squeezed together the flexible bridge sections 102 flex to cause the two opposed fingers 100 to move apart from each other. That action frees the pair of fingers 100 from whatever pair of notches 96 they had been located in so that the slide member 48 can then be slid to any other position with respect to the base member 44, whereupon the pair of fingers are aligned with the pair of notches at that new position. The handles 98 can then be released, causing them to snap back to bring the fingers into those notches to releasably secure the slide in that position.

In order to facilitate usage of the needle guide device 20 to establish a desired angular trajectory for the needle, the device 20 includes indicia to provide an indication of the angle to which the needle guide has been set. In particular, the needle guide includes a plurality of letters, in this exemplary case the letters A through G, located on the front surface of the base member 44. The notches associated with the letters A-G, establish the angles of 45°, 35°, 25°, 20°, 15°, 10°, and 5°, respectively.

It should be pointed out at this juncture that the use of letters to indicate a desired angular orientation for the needle is merely exemplary. Thus, the indicia may be in the form of numerical indicia directly identifying the angle, e.g., indicia stating "40°", or numerical indicia representing a particular angle. Alternatively, the indicia may be in the form of different colors representing different angles or some other indicia representing different angles.

In any case, the top edge portion of the body section 86 includes a pair of windows 104 (FIG. 10) which are configured to expose the particular indicia, e.g., in this example the letters A-G, associated with the pair of notches 96 in which the pair of fingers 100 are located. Thus, the user of the device can press on the handles 98 of the slide member to free its fingers from the base member so that the slide member can be slid with respect to the base member until one of windows 104 exposes the letter (or other indicia) associated with the desired angle for the needle. The handles can then be released to enable the arms to spring back, whereupon the fingers enter the associated notches, thereby releasably locking the slide in that desired position.

It should be noted that while the needle guide device 20 as described above is configured so that the slide can be moved to any of the seven discrete positions established by the pairs of notches 96 to establish the angled needle trajectory associated with that pair of notches, the spring bias provided by the flexible bridge sections 102 will hold the free end of the fingers in sufficient frictional engagement with the side edges 50A and 5B of the base member between the notches 96. Thus, the slide member can be slid and held at a "free hand" position in between any of the notches. This feature is important to enable the user to establish a precise desired needle trajectory angle even if it isn't one of the pre-established angles defined by the pairs of notches.

As discussed above, the needle guide 20 is configured to be directly mounted on an imaging transducer 10 which has been specially constructed or modified to include the heretofore described locating feature (e.g., coupling member 16). The needle guide devices of this invention are also suitable for use on conventional imaging transducers, i.e., imaging transducers without the locating feature or coupling member. To that end, the heretofore mentioned adaptor bracket, constituting another aspect of this invention, is provided. The adaptor bracket 200 is best seen in FIGS. 13-17 and enables a needle guide of this invention to be indirectly mounted on the prior art imaging transducer 10. The adaptor bracket 200 basically comprises a hollow housing 202 made of any suitable material, e.g., a plastic. The housing is hollow and shaped to accommodate the lower portion of whatever prior art imaging transducer it is to be used on. The housing 202 includes a front portion 204 and a rear portion 206 disposed opposite to the front portion. The bottom of the housing is open to expose the working end of the imaging transducer 10. In order to facilitate the disposition of the adaptor bracket 200 on the bottom portion of the conventional imaging transducer, the housing is split to enable the housing to be opened like a clamshell. In particular the housing 202 includes a vertically oriented channel 208 extending from the top edge of the housing at the back portion to approximately the mid-height of the housing. The portion 210 of the housing 202 between the bottom of the channel 208 and the bottom edge of the housing (i.e., the open bottom of the housing) forms the "hinge" of the clamshell arrangement. The front portion 204 of the housing is split in half from its top edge to its bottom edge by means of a top channel 212 and a bottom channel 214. The top channel merges with the bottom channel and is slightly wider than the top channel.

In order to enable a needle guide device constructed in accordance with this invention on the adaptor bracket 200, the front portion of the housing 202 includes a coupling member 216. The coupling member 216 is constructed like the coupling member 16 described heretofore, except that it is split by the channel 214 into two halves. In particular, the coupling member 216 includes one half on one side of the channel 214 and the other half on the other side of that channel. Taken together the two half sections of the coupling member form of a projection of somewhat rectangular profile and having an enlarged top portion 116A and a pair of undercut recesses 116B on the opposed long sides of the projection, i.e., on one side of one half section and on the corresponding side of the other half section.

The mounting of the adaptor bracket 200 can be readily accomplished by grasping portions of the front portion of the housing on opposite sides of the channel 212 to open that channel, whereupon the two portions of the housing on opposite sides of the channel can pivot open about hinge 210 so that the bottom portion of the conventional imaging transducer 10 can be placed between the two open halves of the housing, with the working end of the imaging transducer within the open bottom of the housing. The housing can then be released so that it snaps back into its normally closed state on the imaging transducer like shown in FIG. 14. A cover 14 can then be placed over the adaptor bracket and the transducer. A needle guide device constructed in accordance with this invention can then be releasably mounted on the coupling member as described above with reference to the needle guide 20.

Thus, any existing prior art imaging transducer can be readily retrofit by means of the adaptor 200 to accommodate the needle guide device 20 (or any other needle guide device making use of the lockable mounting member).

Turning now to FIGS. 18-20 and 22-24 the details of the fixed angle needle guide device 20' will now be described. That device makes use of the same lockable mounting member 24 for releasable mounting on the same coupling member 16 or 216 as described heretofore. Thus, in the interest of brevity the common features of those components will be given the same reference numbers and the details of their construction and operation will not be reiterated.

As best seen in FIGS. 12-14 and 16-18, the needle guide device 20' basically comprises a needle guide assembly 122 and the lockable mounting member 24. Those components are each preferably molded of any suitable plastic material. The needle guide assembly 122 basically comprises a base member 126 having a slot or channel 128 extending through it from one side of the base member to the other side. The channel 128 is configured to slidably receive the lockable mounting member 24 in a manner similar to the slot or channel 62 in the adjustable needle guide device 20. The back surface of the base member 126 includes a recess 130.

With the lockable mounting member 24 in place within the slot or channel 128 in its open position, the coupling member 16 of the transducer, with a portion of the cover 14 overlying the top 16A of the coupling 16, can be extended through the recess 130 and through the window 38 in the lockable mounting member. Then the handle 26 of the lockable mounting member can be pushed inward to move the lockable mounting member to the locked position, whereupon the flanged projection 36 is located within the undercut recess 12B of the coupling member 16 or 216 to thereby releasably mounting the needle guide device 20' onto the imaging transducer or on the adaptor bracket with the cover 14 interposed therebetween.

The needle guide assembly also includes a barrel member 132 and a needle holder 134. The barrel member 132 is an elongated generally tubular member having a slot 136 extending parallel to the central longitudinal axis 138 of the barrel member from the top of the barrel member to the bottom thereof. The barrel member is fixedly mounted on the base member 126 so that the longitudinal central axis 138 of the barrel member, which defines the needle trajectory, extends at a predetermined angle to the base member 126. In the exemplary embodiment 20' shown in FIGS. 18-20, 22 and 24 the predetermined angle is 5° in relation to its mounting member 126. In the exemplary embodiment 20" shown in FIGS. 21 and 25 the predetermined angle is 45° in relation to its mounting member 126. The means for mounting the barrel member 132 in its particular angular orientation comprises a pair of arcuate struts 140 projecting outward from the base member 126.

Figure 20:
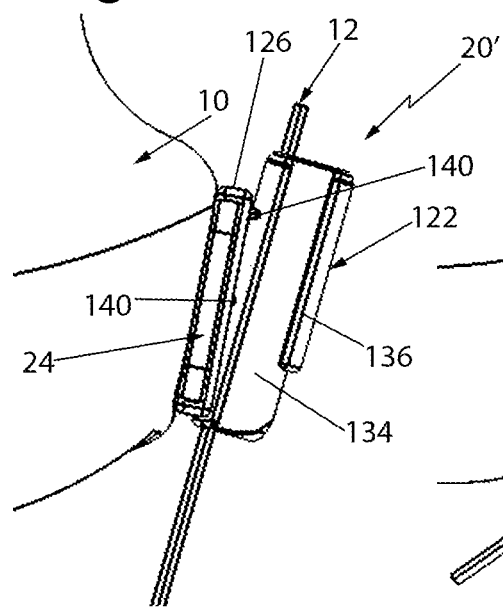
FIG. 20 is a reduced side elevation view of the needle guide device of FIG. 18 shown on the transducer establishing a 0° angle trajectory for the needle.

The needle holder 134 is in the form of an elongated cylindrical insert that is configured to be disposed within the barrel member 132 to directly hold the needle 12 therein. Moreover, the insert is configured to be rotated about the longitudinal central axis 138 of the barrel member between an open position, such as shown in FIG. 24, and a closed position, such as shown in FIGS. 18 and 20, and vice versa. The elongated cylindrical insert has a slot 142 extending parallel to the central longitudinal axis of the insert from one end of the insert to the other. The width of the slot 142 is just slightly larger than the diameter of the particular diameter needle 12 to be used with the needle guide device 20'. The inner end of the slot 142 is circular in shape to accommodate the needle 12 therein. The depth of the slot, i.e., the distance from the outer surface of the insert 134 (and the inner surface of the barrel member 132) to the inner end of the slot is just slightly greater than the diameter of the needle. Thus, when the needle is inserted in the slot 142 and the insert is in the closed position a portion of the periphery of the slot 142 engages a portion of the periphery of the needle 12, while a portion of the inner surface of the barrel member contiguous with the slot engages another portion of the periphery of the needle, thereby holding the needle in place along a path that is parallel to the longitudinal central axis 138 of the needle holder. That path establishes the trajectory for the needle.

As is the case of the adjustable needle guide device 20, different inserts or needle holders can be provided with different size slots 142 to accommodate different diameter needles for use with a fixed angle needle guide device, like device 20'. Moreover, like the needle holder 74 of device 20, the needle holder of device 20' makes use of a slot 142 whose upper end is chamfered to facilitate the axial introduction of the needle therein.

A tab 144 projects radially outward from the top end of the insert 132 to enable the user to rotate the insert about central longitudinal axis 138 within the barrel member 134 between the open and closed positions, and vice versa. In order to accommodate the tab 144 the upper end of the barrel member has an internal T-shaped slot having an elongated portion 146 extending about a portion of the periphery of the barrel member just below the top edge thereof and an entry portion 148 extending from the top edge to the elongated portion 146. The tab 144 includes a narrow section where the tab merges with the tubular insert and which is configured to be introduced through the entry portion 148 of the T-shaped slot and then into the elongated portion of that slot. The elongated portion of the T-shaped slot is of a sufficient length to enable the insert 132 to be rotated about an angle of approximately 180° between the closed position and the open position, and vice versa, when the tab 144 is within the elongated portion 146 of the slot.

It should be pointed out at this juncture that when the needle holder or insert 132 is in the open position, like that shown in FIG. 24, the needle 12 can be inserted therein laterally instead of axially through the chamfered upper end of the insert as discussed above. In particular, the tab is grasped by the user to rotate the insert 180° about central longitudinal axis 138 (which is also the longitudinal central axis of the barrel member) from the position like shown in FIGS. 18 and 19 to the position like shown in FIG. 24. At that time the slot 142 of the insert will be aligned with the slot 136 of the barrel member, whereupon the needle 12 can be inserted laterally through the aligned slots. Once the needle is in the slot 142 the tab 144 can be rotated 180 degrees back to the closed position shown in FIGS. 18 and 19, thereby holding the needle in place.

After the needle has been deployed, i.e., inserted into the patient's body along the desired trajectory, the imaging transducer 10 and needle guide device 20' that is mounted thereon can be freed (removed) from the needle leaving the needle in place by merely rotating the insert 74 to its open position, like shown in FIG. 18, whereupon the transducer and needle guide device can be moved as unit laterally with respect to the needle so that the needle passes through the aligned slots 136 and 142.

In FIG. 21 there is shown an alternative embodiment of a fixed angle needle guide device 20" constructed in accordance with this invention. The needle guide device 20" is virtually identical in construction to the needle guide device 20', except that it establishes a greater angled trajectory for the needle, i.e., a 40° angle with respect to the body member 126. To that end, the struts 140 are of a longer length, e.g., establish an angle of 40°. In the interest of brevity the common features of the embodiments of the devices 20' and 20" will be given the same reference numbers and the details of their construction and operation will not be reiterated.

As mentioned above the subject invention contemplates providing a kit of plural fixed angle needle guide devices, like device 20' and 20" as well as others establishing other fixed angles desired for use.

Like the adjustable needle guide device 20, the fixed angle devices 20', 20' and any other fixed angle device, are configured to be directly mounted on an imaging transducer which has been specially constructed or modified to include the heretofore described locating feature, e.g., the coupling member 16, and with a cover interposed therebetween. For applications making use of a conventional imaging transducer, the bracket or adaptor 200, like shown in FIG. 14, can be used with the fixed angle needle guide device. For example, FIG. 25 shows a conventional imaging transducer 10 on which an adaptor 200, like that described above, has been mounted and over which a conventional cover 14 has been disposed. In that embodiment the fixed needle guide device 20" is releasably mounted to the coupling member 16 of the adaptor, with the cover interposed therebetween.

It should be pointed out at this juncture that various modifications can be made to the structure of the needle guide devices, the coupling members and the adaptor brackets within the scope of this invention. By way of example, and not limitation, the slidable connection between the coupling member of the imaging transducer or the adaptor bracket and the lockable mounting member can be reversed from the exemplary embodiment described above. Thus, instead of the lockable mounting member of the needle guide device having a projection which is configured to be received within a recess in the coupling member of the imaging transducer or the adaptor bracket, the lockable mounting member can make use of a recess, e.g., an undercut recess, while the coupling member can make use of a projection for slidable receipt in the recess of the lockable mounting member. Moreover, the recess on the coupling member or the recess on the lockable mounting member (if the components are reversed) need not be located as shown in the exemplary embodiment, e.g., on the sides of the coupling member, but can be in any suitable location to effect the slidable, releasably locking engagement between the coupling member and the lockable mounting member. Furthermore, the pivotable connection between the slide member and the barrel member can be reversed from the exemplary embodiment described above, i.e., the adjustable angle needle guide can make use of a barrel having at least one projecting fingers and a slide member having an ear with at least one angularly extending track or slot for receipt of the at least one finger. Similarly, the pivotable connection between the slide member and the body member can be reversed from the exemplary embodiment described above, i.e., the barrel member can include a pair of aligned holes and the body member can include a pair of pins for receipt in the aligned holes to enable the barrel member to pivot thereabout.

In view of the foregoing it should be appreciated by those skilled in the art that the common locating feature, e.g., the coupling member, of this invention can be applied to most general purpose ultrasound transducers. That common locating feature can be easily cleaned. Moreover, it is shaped similar to a #1 array indicator, so users of the invention should feel familiar with it. Moreover, the structure and arrangement of the common locating feature causes minimal interference or discomfort during scanning, yet provides stable support of for the needle guide device. Further still, the locating feature allows attachment without damaging an ultrasound cover. Insofar as the needle guide device is concerned, it enables one to fix the trajectory angle of the device and also allows for user selection of multiple trajectories. The device incorporates functionality where the user can change the needle trajectory angle before or after assembly to a transducer, bracket and/or insertion of the needle therein. Further yet, the needle guide device provides visible indicia in the form of a character/number/identification element for each needle path trajectory, allowing the user to identify the trajectory and manually select the corresponding guidelines overlay on the ultrasound system. In accordance with one preferred aspect of the invention the needle guide devices enable the establishment of an angular range of at least 40° and can maintain a close proximity to the transducer to achieve a minimal "blind zone". The needle guide devices of this invention accept multiple versions of inserts sized for differing needle diameters. Whether a fixed angle needle guide device or a variable need guide device, a needle guide device constructed in accordance with this invention exhibits a form factor that is minimal near the transducer lens so as not to interfere with scanning and has a sufficiently low profile without any fixed features that extend past the needle path.

Referring now to FIG. 26 another, and more preferred, exemplary embodiment of a reusable needle guide device 320 constructed in accordance with this invention is shown. The needle guide device 320 is configured to be releasably mounted directly on an imaging instrument, e.g., an ultrasound transducer or probe 10 like shown in FIGS. 26 and 27, or mounted on an adapter bracket 400 constructed in accordance with this invention and shown in FIGS. 43 and 44. In any case the device 320 when mounted on a transducer 10 or on an adaptor 400 which in turn is mounted on a transducer serves to mount and guide a needle 12 or any other elongated instrument through a desired path or trajectory into the body of a patient (human or animal) for a tissue biopsy procedure or any number of other medical procedures.

As will be seen and described in detail later the needle guide device 320 is adjustable, so that it can establish a trajectory path enabling the needle or instrument to reach an internal site in the patient's body that is close to or far away from the distal or working end of the transducer. In particular, the needle guide device 320 is configured to enable the user to adjust the needle angle trajectory through a wide range.

The exemplary needle guide device 320 (and any other needle guide device constructed in accordance with this invention) makes use of a mounting feature to enable it to be readily and quickly mounted on an imaging transducer 10 either with or without a conventional cover 14 interposed therebetween. If a cover is used it will typically be formed of a thin, flexible sheath of any suitable material, e.g., latex, into a suitable shape, e.g., a condom-shaped sheath, to be placed over the imaging transducer before the needle guide device is mounted thereon to keep the transducer sanitary. In the interest of drawing simplicity the cover has been omitted from figures of the drawing of the embodiment 320, it being understood that the cover can be interposed between the needle guide device and the imaging transducer on which the needle guide device is mounted. Alternatively the cover can be interposed between the needle guide device and the adapter bracket on. In either such case the needle device can be releasably mounted without breaching the cover.

The releasably mounting feature of this invention will be described in detail later. Suffice it for now to state that the exemplary needle guide device 320 includes a lockable mounting assembly arranged to be releasably secured to a universal or common locating feature or coupling member that is provided on the housing of a specially constructed imaging transducer or on an adapter bracket for use on a conventional imaging transducer. The lockable mounting assembly includes a slidable member (e.g., a lock slide to be described later) that is configured to be slid from an unlocked position to enable the needle guide device to be mounted on the coupling member, to a locked position wherein the needle guide is releasably locked or secured to the coupling member and hence to the transducer.

As will also be described later the needle guide device 320 (and all other needle guides constructed in accordance with subject invention) is configured to enable the user to adjust the angle of penetration for the needle between a minimum angle and a maximum angle. When adjusted to the maximum angle the needle guide device enables a very shallow depth of penetration for the needle, with a minimal blind spot, without any portion of the needle guide device projecting far out from the transducer to block the view of the user. Thus, the needle guide device 320, like other needle guide devices of this invention, has a compact form factor.

Turning now to FIGS. 26, 27 and 31 it can be seen that the exemplary needle guide device 320 basically comprises a needle guide assembly 322 and a lockable mounting assembly 324. The lockable mounting assembly 324 is configured to be releasably secured to a universal or common locating coupling member 316 that is located on the housing of the transducer adjacent the distal or working end of the transducer. The coupling member 316 is preferably mounted at the location of the typical "#1 array indicator" of a conventional ultrasonic transducer. In the case where the common locating coupling member 316 is used on an adapter bracket 400, it will be located on that bracket at a position corresponding to the position that the coupling member is mounted on the transducer itself.

As best seen in FIGS. 28-31 the coupling member 16 is in the form of a projection of somewhat regular profile and having an enlarged generally planar front surface portion 316A, an undercut recesses 316B on the left side of the projection, an undercut recess 316C on the right side of the projection, and an undercut recess 316D on the top side of the projection. As best seen in FIG. 30, the undercut recess 316D slants downward symmetrically from the center of the top side towards the left side of the projection and also toward the right side of the projection.

The lockable mounting assembly 324 is best seen in FIGS. 32-36B and basically comprises a slidable member or lock slide 310 and a lock lever 312. Each is molded of a suitable plastic material. The lock slide 310 is a generally planar frame-like member having a generally linear side surface 310A and a pair of projecting ears 310B and 310C (FIG. 34) located on opposite sides of the surface 310A. The surface 310A constitutes an engagement surface configured to mate with (be received within) the left side undercut recess 316C of the projection 316 when the lockable mounting assembly is in the locked position. The lock slide includes an opening 310D for receipt of portions of the lock lever 312 (to be described later). The lock slide is arranged for slidable receipt within an undercut slot 302 in a body or base member 304 of the needle guide device to enable the lock slide to be slid between the unlocked position (not shown) and the locked position (FIG. 33), and vice versa. The body or base member 304 of the needle guide device forms a portion of the needle guide assembly 322. As best seen in FIG. 34 the undercut slot 302 includes short front edge surface 302A and an opposed pair of linear surfaces 302B and 302C which between them define the entryway to the undercut slot. The end of the slot opposite the slot's entryway is in the form of a generally planar, linear projection 306 overlying the slot. The ears 310B and 310C of the lock slide are configured to be introduced into the undercut slot by locating them within the portions of the slot contiguous with the surfaces 302B and 303C, respectively, and then sliding the lock slide towards projection 306. The projection 306 forms a stop surface which is configured to mate with (be received within) the right side undercut recess 316C of the coupling member (projection) 316 when the lockable mounting assembly is in the locked position, whereupon the projection 316 is tightly sandwiched between the engagement surface 310A and the stop surface 306.

The means for sliding the lock slide 310 between the unlocked position and the locked position, and vice versa, is the heretofore identified lock lever 312. As can be seen in FIGS. 35, 36A and 36B the lock lever 312 basically comprises a finger grip portion 312A, a pivot pin portion 312B (FIG. 36B), and a cam portion 312C. The pivot pin 312B is a split member of circular profile having an enlarged head 312D at the free end thereof. A small tab 312E projects outward from the head 312D. As best seen in FIG. 36A the cam 312C is laterally offset from the central axis of the pivot pin 312B. The cam 312C is configured to be located within the opening 310D of the lock slide 310, with the pivot pin 312B being located within a hole 304A in a projecting portion 304B of the body member 304 adjacent the slot 302 and with the head 312D of the pivot pin located on the opposite side of the projection 304B as the slot 302. The hole includes a recess 304C (FIGS. 32 and 34) which is provided for the purpose of providing an opening to allow tab 312E to fit through. The tab 312E is configured to fit through the recess 304C.

The pivot pin 312B is arranged to be pivoted within the hole 304A about its central axis by the finger grip 312A to cause the cam 31C to engage portions of the lock slide to move it to either the locked or unlocked positions, depending upon the direction of notation of the pivot pin 312B. In particular, since the cam 312C is laterally offset from the central axis of the pivot pin 312B, and since the cam is located within the opening 310D of the lock slide 310, the pressing downward on the finger grip 312A effects the clockwise rotation of the pivot pin, whereupon a portion of the surface of the cam pushes on a portion of the slide lock contiguous with the opening 310D towards the stop surface 306 to the locked position. Conversely, pressing upward on the finger grip effects the counter-clockwise rotation of the pivot pin, whereupon a portion of the surface of the cam pushes on a diametrically opposed portion of the slide lock contiguous with the opening 310D away from the stop surface 306 to move the slide lock to the unlocked position.

The releasable mounting of the needle guide device 320 onto a transducer having a coupling member 316 or onto an adapter bracket 400 including a similarly constructed coupling member is achieved as follows. The finger grip 312A of the lock lever 312 is pressed upward to move the slide lock to the unlocked or open position (if the slide lock is not already in that position). The needle guide device 320 and the transducer or adapter bracket 400 are then moved relative to each other so that the coupling member or projection 316 is located within the undercut slot 302 between the engagement surface 310A and the stop surface 306. Once that has been accomplished the finger grip 312A of the lock lever is pressed downward, to cause the cam 312C to engage a portion of the slide lock 310 contiguous with the opening 310D to slide the slide lock towards the stop surface 306, whereupon the stop surface is located within the right side recess 316C of the projection and the engagement surface 310 of the slide lock is located in the left side recess 316B of the projection whereupon the coupling member 316 is tightly sandwiched between the engagement surface 310A and the stop surface 306. This action effectively releasably secures the needle guide device onto the transducer or adapter bracket so that it is ready for use. To remove the needle guide device from the transducer or adapter bracket, when such is desired, all that is required is to press upward on the finger grip 312A of the lock lever to cause the cam 312B to engage a diametrically opposed portion of the slide lock contiguous with the opening 310D to slide the slide lock away from the stop surface 306, thereby freeing the coupling member 316 so that it can be removed from the undercut slot 302.

Referring now to FIGS. 31, 37-42 the details of the needle guide assembly 322 will now be described. To that end, it basically comprises the heretofore identified body or base member 304, a needle holder subassembly 346 and a slide member 348. Each is molded of a suitable plastic material. The body member 304 comprises a generally flat panel having a pair of long sides 350A and 350B. A pair of triangularly shaped flanges 352A and 52B project rearwardly from the bottom portions of the sides 350A and 350B, respectively. The inner surface of each flange includes a short slot terminating in a circular hole 354 for accommodating a respective pivot pin of a cylindrically shaped barrel member 356 (to be described shortly) forming a portion of the needle holder subassembly 346. The holes 354 are axially aligned. The front portion of the body member 304 includes an arcuate recess or cavity 360, as best seen in FIGS. 32 and 40, which is configured to accommodate the barrel member 356.

The barrel member 356 forms a portion of the needle holder subassembly 346 and is an elongated generally tubular member having a centrally located linear front slot 366 (FIG. 41) extending parallel to the central longitudinal axis of the barrel member. A pair of triangular ears 368 project outward from the barrel member 356 on opposite sides of the slot 366. Each ear 368 includes a linear slot or track 370 which extends at an acute angle, e.g., 15°, from the longitudinal axis of the barrel member, and oriented upward and outward as shown in FIGS. 31, 39 and 141. As best seen in FIG. 41, the bottom edge portion of the barrel member includes a pair of axially aligned pivot pins 372 projecting outward therefrom (although only one the pins can be seen). The pins 372 are configured to be disposed within respective holes 354 in the body member 304. When so located the barrel member is able to pivot with respect to the body member about the axis of the aligned holes to enable the barrel to assume any desired angular position with respect to the body member from 0° (as shown in FIGS. 26 and 27) to 40° (as shown in FIGS. 27 and 38). The means for effecting the pivoting of the barrel member with respect to the base member is the heretofore identified slide member 248.

Before describing the slide member 248, a description of the member for holding the needle 12 in the needle guide device 320 is in order. That member forms a portion of the needle holder subassembly 346 and is best seen in FIG. 41. It is in the form of an elongated cylindrical needle holder or insert 374. The insert is molded of any suitable plastic material and is configured to be disposed within the barrel member 346 to directly hold the needle 12 therein. Moreover, as will be seen and described later, the insert 374 is configured to be rotated about the central longitudinal axis 378 of the barrel member between an open position, such as shown in FIG. 41, and a closed position, such as shown in FIGS. 33 and 39, and vice versa. The insert 374 has a slot 376 extending parallel to the central longitudinal axis of the insert from one end of the insert to the other. The width of the slot 376 is just slightly larger than the diameter of the particular diameter needle 12 to be used with the needle guide device. The inner end of the slot 376 extends parallel to the central longitudinal axis of the insert and is circular in shape to accommodate the needle 12 therein. The depth of the slot, i.e., the distance from the outer surface of the insert (and the inner surface of the barrel member) to the inner end of the slot is just slightly larger than the diameter of the needle. Thus, when the needle is inserted in the slot 376 a portion of the periphery of the slot at the inner end engages the needle, while a portion of the inner surface of the barrel member contiguous with the slot engages another portion of the periphery of the needle, thereby holding the needle in place along a path whose longitudinal axis 378 is parallel to but slightly laterally offset from the central longitudinal axis of the needle holder. That path establishes the trajectory for the needle. The upper or entrance end of the slot 376 is chamfered or tapered to facilitate the axial introduction of the needle therein, i.e., the tapered or chamfered surface directs the distal end of the needle towards the slot when the needle is introduced axially.

It should be pointed out at this juncture that different inserts with different size slots 376 can be provided in lieu of the insert shown herein to accommodate different diameter needles.

A tab 82 projects radially outward from the top end of the insert to enable the user to rotate the insert 376 about central longitudinal axis of the barrel member within the barrel member between the open and closed positions. In order to accommodate the tab 382 the upper end of the barrel member has a pair of notches 384 immediately adjacent each side of the slot 366. The ends of the notches establish a pair of stops enabling the insert to be rotated through an angle of 180 degrees and no more.

When the needle holder or insert 374 is in the open position the slot 376 of the needle holder is aligned with the slot 266 of the barrel member the needle 12 can be inserted laterally through the aligned slots, instead of axially through the chamfered upper end of the needle holder as discussed above. To that end, the tab 382 is grasped by the user to rotate the needle holder 180° about central longitudinal axis 378 (which is also the longitudinal central axis of the barrel member) from the closed position shown in FIGS. 31 and 39 to a position like shown in FIG. 41 where the slots 376 and 366 are aligned, whereupon the needle can be inserted laterally through the aligned slots. Once the needle is in the slot 376 along axis 378, the tab 382 can be rotated 180° back to the closed position shown in FIGS. 6 and 14, thereby holding the needle in place.

As will be appreciated by one skilled in the art, after the needle has been deployed, i.e., inserted into the patient's body along the desired path or trajectory, the imaging transducer 10 and needle guide device 20 can be freed (removed) from the needle leaving the needle 12 in place by merely rotating the insert 374 to its open position, whereupon the imaging transducer 10 and needle guide device 320 mounted thereon can be moved as a unit laterally with respect to the needle 12 so that the needle passes through the aligned slots 376 and 366.

Turning now to FIGS. 6, 15 and 16 the details of the construction and operation of the slide member 348 to pivot the needle holder assembly to the desired angle will be described. The slide member basically comprises a generally planar body section 386 having a pair of side flanges 388 projecting backward from respective side edges of the body section 386. Each flange 388 includes a longitudinally extending slot or channel 388A (FIG. 31) for receipt of a respective side edge 350A or 350B of the base member 304 to slidably mount the slide member on the base member. The central portion of the body section 386 includes a recess or cavity 390 to accommodate the barrel member 346 when it is in its 0° orientation, i.e., when the slot 376 of the needle holder mounted within the barrel member extends parallel to the plane of the undercut slot 302 of the base member 304. A pair of ears 392 project outward perpendicularly from the lower portion of the body section 386 on each side of the slot 390. Each ear terminates in a free end from which a pivot pin 394 projects. The pivot pins 394 are axially aligned and each is configured to be disposed within a respective one of the angularly extending tracks 370 of the barrel member.

When the slide member 348 is its upper-most position with respect to the base member 304, the pivot pins 394 of the slide member will be at the upper ends of the tracks 370 of the barrel member, whereupon the barrel member will be pivoted about its pivot pins 372 to the 0° angular orientation shown in FIGS. 26 and 37. Conversely, when the slide member 348 is its lower-most position with respect to the base member 304, the pivot pins 394 of the slide member will be at the lower ends of the tracks 370 of the barrel member, whereupon the barrel member will be pivoted about its pivot pins 372 to the 40° angular orientation shown in FIGS. 27 and 38.

The exemplary embodiment of the variable angle needle guide device 320 shown herein includes a locking mechanism to hold the barrel member in any one of a number, e.g., five, discrete distinct predetermined angular orientations with respect to the base member, so that the slide member can be readily and repeatedly slid to any one of those positions and to be held against accidental displacement therefrom. The locking mechanism basically comprises a plurality of notches 396 (FIGS. 39 and 40) and a slide lock 398. The notches 396 extend along the side 350B of the base member 304 at various predetermined spaced locations therealong. Each notch is configured to be engaged by the slide lock 398 to hold the slide member at the position established by the selected notch. The slide lock is slidably mounted on the slide member via a flanged rail 330 (FIGS. 40 and 41) extending along the ear 392 adjacent the right side of the slide member. The flanged rail is configured for slidable receipt in the slide lock. The slide lock is best seen in FIGS. 41 and 42 and basically comprises a member having a somewhat hollow body including a T-shaped slot 398A in the bottom portion thereof and a L-shaped flange 398B projecting outward from the inner end of the slide lock. The T-shaped slot is arranged to receive the flanged rail 330 (FIG. 40) of the slide member to enable the slide lock to be slid therealong from an unlocked or retracted position to a locked or extended position, and vice versa. A slot 386A is located adjacent the flanged rail 330 and extends through the channel 388A. When the slide lock is in the extended or locked position the upper section of the L-shaped flange 398B will extend through the slot 386A for disposition in any one of the notches 396 to thereby hold the slide member 348 in place with respect to the body member 304. When the slide member is in the retracted or unlocked position, the upper section of the L-shaped flange 398B will be located outside all of the notches so that the slide member can be slid up or down the body member to any desired position therealong. The slide lock includes a detent mechanism to ensure that the slide lock does not become disconnected from the flanged rail when it is in the refracted position.

In order to facilitate usage of the needle guide device 320 to establish a desired angular trajectory for the needle, the device 320 includes indicia to provide an indication of the angle to which the needle guide has been set. In particular, the needle guide includes a plurality of letters, in this exemplary case the letters A through E, located on the front surface of the base member 304. The notches associated with the letters A-E, establish the angles of 40°, 28°, 18°, 9°, and 3°, respectively.

It should be pointed out at this juncture that the use of letters to indicate a desired angular orientation for the needle is merely exemplary. Thus, the indicia may be in the form of numerical indicia directly identifying the angle, e.g., indicia stating "28°", or numerical indicia representing a particular angle. Alternatively, the indicia may be in the form of different colors representing different angles or some other indicia representing different angles.

In any case, the body section 386 includes a window 332 (FIGS. 39-41) which is configured to expose the particular indicia, e.g., in this example the letters A-E, associated with the notches 396 in which slide lock's L-shaped flange is located. Thus, the user of the device can press on the top surface of the slide lock to slide it to the refracted or unlocked position to free it from the base member so that the slide member can be slid with respect to the base member until the window 332 exposes the letter (or other indicia) associated with the desired angle for the needle. The slide lock can then be slid back to the extended or locked position, whereupon the upper section of the L-shaped flange 398B enters the associated notch 396, thereby releasably locking the slide member in that desired position.

It should be pointed out at this juncture that the needle guide device 320 can be used to establish an angular orientation for the needle that is different than the predetermined angles established by the notches 396, since the construction of the slide member is such that it is continuously slidable with respect to the base member to any position between discrete positions established by those notches. In such a case, all that the user has to do is slide the slide member to the desired position along the base member to establish a desired angle for the needle while keeping the slide lock 398 in its retracted or unlocked position. When the slide lock is in the unlocked position, the upper section of the L-shaped flange 398B will be located outside all of the notches so that the slide member will effectively be floating and can be slid up or down the body member to any desired position therealong to establish any desired angle for the needle. Thus, the needle guide device 320, and other needle guide devices constructed in accordance with this invention, can be used to guide needles or other elongated instruments within the center elevation plane of the transducer allowing free angle movement in relation to the center azimuth plane of the transducer by leaving the slide lock in the unlocked position.

As discussed above, the needle guide 320 is configured to be directly mounted on an imaging transducer 10 which has been specially constructed or modified to include the heretofore described locating feature (e.g., the coupling member 316). The needle guide devices of this invention are also suitable for use on conventional imaging transducers, i.e., imaging transducers without the locating feature or coupling member. To that end, the heretofore mentioned adaptor bracket 400, constituting another aspect of this invention, is provided. The adaptor bracket 400 is best seen in FIGS. 43 and 44 and enables a needle guide device of this invention to be indirectly mounted on any prior art imaging transducer. To that end, the adaptor bracket 400 basically comprises a hollow housing 402 made of any suitable material, e.g., a plastic. The housing is hollow shaped to accommodate the lower portion of whatever prior art imaging transducer it is to be used on. The housing 402 includes a front portion 404 (FIG. 43) and a rear portion 406 (FIG. 44) disposed opposite to the front portion. The bottom of the housing is open at 408 to expose the working end of a conventional imaging transducer 10. In order to facilitate the disposition of the adaptor bracket 400 on the bottom portion of the imaging transducer, the housing is split to enable it to be opened like a clamshell. In particular, the housing 402 includes a vertically oriented channel 410 extending from the top edge of the housing at the back portion to approximately the mid-height of the housing. The portion of the housing between the bottom of the channel 410 and the bottom edge of the housing (i.e., the open bottom 408) forms the "hinge" of the clamshell arrangement. The front portion 404 of the housing is split in half from its top edge to its bottom edge by means of a top channel 412A and a contiguous bottom channel 412B. The top channel is aligned with and merges with the bottom channel and is slightly wider than the bottom channel.

In order to enable a needle guide device constructed in accordance with this invention to be releasably mounted on the adaptor bracket 400, the front portion 404 of the housing 402 includes a locating feature of coupling member like that described previously. In particular the coupling member of the adaptor bracket 410 is constructed like the coupling member 316 described heretofore, except that it is split by the lower channel 412B into two halves, i.e., a left half and a right half. In particular, the coupling member 316 includes one half on one side of the channel 412B and the other half on the other side of that channel. Taken together the two half sections of the coupling member 316 form of a projection of the same shape as described earlier with respect to the coupling member forming a part of the transducer housing.

The mounting of the adaptor bracket 400 on a conventional transducer 10 can be readily accomplished by grasping portions of the front portion 404 of the housing 402 on opposite sides of the channels 412A and 412B to open those channels, whereupon the two portions of the housing 402 on opposite sides of the channel can pivot open like the opening of a clamshell so that the bottom portion of the conventional imaging transducer 10 can be placed between the two open halves of the housing, with the working end of the imaging transducer within the open bottom of the housing. The housing can then be released so that it snaps back into its normally closed state on the imaging transducer like shown in FIG. 43. If desired a cover (not shown) can then be placed over the adaptor bracket and the transducer. A needle guide device constructed in accordance with this invention can then be releasably mounted on the coupling member as described above.

It should thus be apparent to those skilled in the art that any existing prior art imaging transducer can be readily retrofit by means of the adaptor 400 to accommodate the needle guide device 320 (or any other needle guide device in accordance with this invention).

Various modifications can be made to the structure of the needle guide devices, the coupling members and the adaptor brackets within the scope of this invention. By way of example, and not limitation, the slidable connection between the coupling member of the imaging transducer or the adaptor bracket and the lockable mounting member can be reversed from the exemplary embodiment described above. Thus, instead of the slide lock member 310 of the needle guide device having a projection which is configured to be received within a recess in the left side of the coupling member of the imaging transducer or the adaptor bracket, the slide lock can make use of a recess, e.g., an undercut recess, while the left side of coupling member can make use of a projection for slidable receipt in the recess of the slide lock. So too, the projection or stop 306 can be in the form of a recess at its free end, while the right side of coupling member includes a projection for receipt in the stop 306, so long as the coupling member is tightly sandwiched between opposing surfaces to releasably secure the needle guide device onto the coupling member. Furthermore, the pivotable connection between the slide member and the barrel member can be reversed from the exemplary embodiment described above, i.e., the adjustable angle needle guide can make use of a barrel having at least one projecting fingers and a slide member having an ear with at least one angularly extending track or slot for receipt of the at least one finger. Similarly, the pivotable connection between the slide member and the body member can be reversed from the exemplary embodiment described above, i.e., the barrel member can include a pair of aligned holes and the body member can include a pair of pins for receipt in the aligned holes to enable the barrel member to pivot thereabout.

In view of the foregoing it should be appreciated by those skilled in the art that the common locating feature, e.g., the coupling member, of this invention can be applied to most general purpose ultrasound transducers. That common locating feature can be easily cleaned. Moreover, it is shaped similar to a #1 array indicator, so users of the invention should feel familiar with it. Moreover, the structure and arrangement of the common locating feature causes minimal interference or discomfort during scanning, yet provides stable support of for the needle guide device. Further still, the locating feature allows attachment without damaging an ultrasound cover, if such is used.

Insofar as the needle guide device is concerned, it enables one to fix the trajectory angle of the device and also allows for user selection of multiple trajectories. The device incorporates functionality where the user can change the needle trajectory angle before or after assembly to a transducer, bracket and/or insertion of the needle therein.

Further yet, the needle guide device provides visible indicia in the form of a character/number/identification element for each needle path trajectory, allowing the user to identify the trajectory and manually select the corresponding guidelines overlay on the ultrasound system. In accordance with one preferred aspect of the invention the needle guide devices enable the establishment of an angular range of at least 40° and can maintain a close proximity to the transducer to achieve a minimal "blind zone". The needle guide devices of this invention accept multiple versions of inserts sized for differing needle diameters. Further still, needle guide devices constructed in accordance with this invention exhibit a form factor that is minimal near the transducer lens so as not to interfere with scanning and has a sufficiently low profile without any fixed features that extend past the needle path.

Without further elaboration the foregoing will so fully illustrate my invention that others may, by applying current or future knowledge, adopt the same for use under various conditions of service.

What is claimed is:

1. A needle guide device configured for releasable mounting on an imaging transducer or on an adaptor on an imaging transducer, the imaging transducer or the adaptor including a coupling member comprising a rectangular portion projecting outwardly from the imaging transducer or the adapter, wherein the rectangular portion includes first and second undercut recesses on opposing sides of the rectangular portion, said needle guide device comprising:
    a lockable mounting assembly; and a needle guide assembly coupled to the lockable mounting assembly to retain a needle at a desired trajectory with respect to the imaging transducer,
wherein said needle guide assembly comprises:
a body member, and
a needle holder,
said body member comprising a recess for receiving the coupling member therein, wherein the recess comprises a stop portion configured to engage the first undercut recess in the coupling member when the needle guide device is locked to the imaging transducer or the adaptor,
wherein said lockable mounting assembly comprises:
a slidable member having an engagement portion configured to engage the second undercut recess when the needle guide device is locked to the imaging transducer or the adaptor, and
a cam portion coupled to the slidable member and the body member via a pivot pin, wherein the cam portion is laterally offset from a central axis of the pivot pin, such that rotation of the cam portion about the pivot pin causes the slidable member to slide laterally relative to the stop portion in the body member between the locked and unlocked positions,
said lockable mounting assembly being configured to be slidably coupled to said body member and slidable from an unlocked position to a locked position and vice versa, such that when moved from the unlocked position to the locked position, the stop portion of the body member engages the first undercut recess and the engagement portion of the slidable member engages the second undercut portion to clampingly secure the needle guide device to the coupling member.

2. The needle guide device of claim 1, wherein said body member comprises a slot positioned adjacent to said recess for receiving at least a portion of said slidable member.

3. The needle guide device of claim 1, wherein said needle holder is adjustably mounted on said body member to enable said needle holder to be oriented to various selected orientations with respect to said body member to establish various angled trajectories for the needle.

4. The needle guide device of claim 3, wherein said needle guide assembly further comprises:
a needle holder subassembly, and
a slide member,
wherein said needle holder subassembly comprises:
a barrel member, and
said needle holder, said needle holder being located within said barrel member, said barrel member being pivotably mounted on said body member,
wherein said slide member is slidable with respect to said body member, in a plane parallel to a plane of a front surface of said body member, and is further coupled to said barrel member to pivot said barrel member with respect to said body member to a first angular orientation when said slide member is slid to a first position, and to pivot said barrel portion with respect to said body member to a second angular orientation when said slide member is slid to a second position,
wherein said needle holder establishes a first angular trajectory for the needle when said barrel member is in said first angular orientation and a second angular trajectory for the needle when said barrel member is in said second angular orientation,
wherein said second angular trajectory is different than said first angular trajectory.

5. The needle guide device of claim 4, wherein said barrel member is pivotable with respect to said body member through an angle of approximately 40 degrees to establish an angular range of trajectories for the needle from 0 degrees to approximately 40 degrees with respect to said body member.

6. The needle guide device of claim 4,
wherein said slide member includes at least one projecting ear having a free end,
wherein said barrel member comprises a recessed track oriented angularly with respect to a longitudinal axis of the barrel member,
wherein said free end of said projecting ear is slidably coupled to said recessed track, whereupon sliding of said slide member with respect to said body member causes said free end of said projecting ear to slide within said angularly oriented recessed track to pivot said barrel member with respect to said body member.

7. The needle guide device of claim 4, wherein said slide member is slidable to more than two distinct predetermined positions with respect to said body member to establish multiple predetermined angular orientations for the needle.

8. The needle guide device of claim 4, including indicia, one of said indicia being visible when said slide member is in said first position to enable the user to confirm the location of said slide at said first position, another of said indicia being visible when said slide member is in said second position to enable the user to confirm the location of said slide at said second position.

9. The needle guide device of claim 4,
wherein said barrel member comprises a cylindrical cavity having a longitudinal central axis and wherein said needle holder comprises an elongated cylindrical member located within said cylindrical cavity and rotatable about said longitudinal central axis, said needle holder having a passageway extending therethrough parallel to said longitudinal central axis, said passageway being configured for receipt of the needle therein to establish the needle's trajectory.

10. A needle guide device, comprising:
a lockable mounting assembly configured for coupling to an imaging transducer; and
a needle guide assembly coupled to the lockable mounting assembly to retain a needle at a desired trajectory with respect to the imaging transducer,
wherein the needle guide assembly, comprises:
a body member,
a needle holder subassembly, and
a slide member,
wherein said needle holder subassembly comprises:
a barrel member, and
a needle holder, said needle holder being located in said barrel member, said barrel member being pivotably mounted on said body member,
wherein said slide member is slidable with respect to said body member, in a plane parallel to a plane of the body member, and is further coupled to said barrel member to pivot said barrel member with respect to said body member to a first angular orientation when said slide member is slid to a first position, and to pivot said barrel portion with respect to said body member to a second angular orientation when said slide member is slid to a second position,
wherein said barrel member comprises a cylindrical cavity having a longitudinal central axis and wherein said needle holder comprises an elongated cylindrical member located within said cylindrical cavity and rotatable about said longitudinal central axis, said needle holder having a passageway extending therethrough parallel to said longitudinal central axis, and said passageway being configured for receipt of the needle therein to establish the needle's trajectory, wherein said barrel member includes a slot in communication with said cylindrical cavity and extending parallel and to said longitudinal central axis and wherein said needle holder comprises a slot in communication with said passageway, said needle holder being rotatable within said cylindrical cavity between a closed and open position and vice versa, said slot in said needle holder being aligned with said slot in said barrel ember when said needle holder is rotated to said open position wherein a needle extending through said passageway can be removed from said needle holder laterally through said aligned slots and a needle can be introduced into said passageway laterally through said aligned slots, said slots being unaligned when said needle holder is in said closed position, whereupon a needle disposed in said passageway is held therein.

* * * * *

UNITED STATES PATENT AND TRADEMARK OFFICE
CERTIFICATE OF CORRECTION

PATENT NO. : 10,507,038 B2
APPLICATION NO. : 14/930077
DATED : December 17, 2019
INVENTOR(S) : Craig Joseph Cermak It is certified that error appears in the above-identified patent and that said Letters Patent is hereby corrected as shown below:

In the Claims

In Claim 10, at Column 29, Line 16, replace "barrel ember" with "barrel member"

Signed and Sealed this
Seventeenth Day of March, 2020

Andrei Iancu
*Director of the United States Patent and Trademark Office*